(12) United States Patent
Al-Hendy et al.

(10) Patent No.: US 9,790,562 B2
(45) Date of Patent: Oct. 17, 2017

(54) COMPOSITIONS AND METHODS FOR THE DETECTION OR TREATMENT OF UTERINE LEIOMYOSARCOMA

(71) Applicant: Augusta University Research Institute, Inc., Augusta, GA (US)

(72) Inventors: Ayman Al-Hendy, Augusta, GA (US); Mostafa Khater, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 15/282,217

(22) Filed: Sep. 30, 2016

(65) Prior Publication Data
US 2017/0088905 A1  Mar. 30, 2017

Related U.S. Application Data

(60) Provisional application No. 62/235,104, filed on Sep. 30, 2015.

(51) Int. Cl.
| | |
|---|---|
| *C12Q 1/68* | (2006.01) |
| *C12N 7/00* | (2006.01) |
| *A61K 48/00* | (2006.01) |

(52) U.S. Cl.
CPC ........ *C12Q 1/6897* (2013.01); *A61K 48/0058* (2013.01); *C12N 7/00* (2013.01); *C12Q 1/6886* (2013.01); *C12N 2710/10343* (2013.01); *C12Q 2600/158* (2013.01)

(58) Field of Classification Search
None
See application file for complete search history.

(56) References Cited

PUBLICATIONS

Taubert et al.; Expression of survivin detected by immunohistochemistry in the cytoplasm and in the nucleus is associated with prognosis of leiomyosarcoma and synovial sarcoma patients; BMC Cancer; (2010) 10:65; pp. 1-7.*
Al-Hendy, A., et al., "Ovarian Cancer Gene Therapy: Repeated Treatment with Thymidine Kinase in an Adenovirus Vector and Ganciclovir Improves Survival in a Novel Immunocompetent Murine Model", Am J Obstet Gynecol, 182(3): 553-559 (2000).
Al-Hendy, A., et al., "Gene Therapy of Uterine Leiomyomas: Adenovirus-Mediated Expression of Dominant Negative Estrogen Receptor Inhibits Tumor Growth in Nude Mice", Am J Obstet Gynecol, 191(5): 1621-1631 (2004).
Altieri, et al., "Transcriptional Analysis of Human Survivin Gene Expression", Biochem. J, 344:305-311 (1999).
Baird, D, et al., "High Cumulative Incidence of Uterine Leiomyoma in Black and White Women: Ultrasound Evidence", Am J Obstet Gynecol, 188(1):100-107 (2003).
Barker, S.D. et al., "Combined Transcriptional and Transductional Targeting Improves the Specificity and Efficacy of Adenoviral Gene Delivery to Ovarian Carcinoma", Gene Ther 10(14): 1198-1204 (2003).
Breidenbach, M. et al., "A New Targeting Approach for Breast Cancer Gene Therapy Using the Heparanase Promoter", Cancer Lett 240(1): 114-122 (2005).
Brooks, S.E., et al., "Surveillance, Epidemiology, and End Results Analysis of 2677 Cases of Uterine Sarcoma 1989-1999", Gynecol Oncol 93(1): 204-208 (2004).
Buttram, V.C., Jr. et al., "Uterine Leiomyomata: Etiology, Symptomatology, and Management", Fertil Steril, 36(4): 433-445 (1981).
Carney, M.E., "Gynecologic Cancers", Hawaii Med J 61(12): 283-286 (2002).
Etzioni, R., et al., "The Case for Early Detection", Nat Rev Cancer, 3(4): 243-252 (2003).
Franklin, R.J., et al., "Adenoviral Vectors for In Vivo Gene Delivery to Oligodendrocytes: Transgene Expression and Cytopathic Consequences", Gene Ther 6(8): 1360-1367 (1999).
He, T., et al., "A Simplified System for Generating Recombinant Adenoviruses", Proc Natl Acad Sci U.S.A., 95 (5):2509-14 (1998).
Houdt, W., et al., "The Human Survivin Promoter: A Novel Transcriptional Targeting Strategy for Treatment of Glioma", J. Neurosurg, 104:583-592 (2006).
Krasnykh, V. N., et al., "Generation of Recombinant Adenovirus Vectors with Modified Fibers for Altering Viral Tropism", J Virol 70(10): 6839-6846 (1996).
Li, F, et al., "Transcriptional Analysis of Human Survivin Gene Expression", Biochem. J, 344:305-311 (1999).
Rauk, P.N., et al, "Mitogenic Effect of Basic Fibroblast Growth Factor and Estradiol on Cultured Human Myometrial and Leiomyoma Cells", Am JH Obstet Gynecol 173(2): 571-577 (1995).
Reynolds, P.N., et al., "Combined Transductional and Transcriptional Targeting Improves the Specificity of Transgene Expression in Vivo", Nat Biotech, 19(9): 838-842 (2001).
Serden, S.P., et al., "Treatment of Abnormal Uterine Bleeding with the Gynecologic Resectoscope", J Reprod Med, 36(10): 697-699 (1991).
Van Houdt, W. J., et al., "The Human Survivin Promoter: A Novel Transcriptional Targeting Strategy for Treatment of Glioma", J Neurosurg 104(4): 583-592 (2006).
Zhu, Z., et al., "Transcriptional Targeting of Tumors with a Novel Tumor-Specific Survivin Promoter", Cancer Gene Therapy, 11:256-262 (2004).

* cited by examiner

*Primary Examiner* — Antonio Galisteo Gonzalez
(74) *Attorney, Agent, or Firm* — Smith, Gambrell & Russell, LLP; Charles Vorndran

(57) ABSTRACT

Compositions and methods for the detection and treatment of cancer are provided. It has been discovered that uterine cancer cells selectively induce the survivin promoter to express a gene product. One embodiment provides a method for detecting uterine malignancy by systemic administration of a cancer-specific vector that utilizes a Survivin promoter to drive expression of a reporter gene. The expression of the reporter gene is detectable exclusively in malignant cells, for example using conventional imagining techniques.

5 Claims, 5 Drawing Sheets

US 9,790,562 B2

COMPOSITIONS AND METHODS FOR THE DETECTION OR TREATMENT OF UTERINE LEIOMYOSARCOMA

FIELD OF THE INVENTION

The invention is generally directed to molecular biology, more particularly to the detection and treatment of cancer using nucleic acid constructs.

REFERENCE TO THE SEQUENCE LISTING

The Sequence Listing submitted as a text file named "GRU_2016_004_ST25.txt," created on Sep. 30, 2016, and having a size of 27,881 bytes is hereby incorporated by reference pursuant to 37 C.F.R. §1.52(e)(5).

BACKGROUND OF THE INVENTION

Benign uterine leiomyomas (fibroids) are the most common pelvic tumor in women (estimated lifetime risk of 70 percent in white women and 80 percent in black women) (Buttram, V. C., Jr. and R. C. Reiter, Fertil Steril, 36(4): 433-445 (1981); Serden, S. P. and P. G. Brooks, J Reprod Med, 36(10): 697-699 (1991); Baird, D. et al., Am J Obstet Gynecol, 188(1):100-107 (2003)). Uterine sarcoma is rare (3 to 7 per 100,000 in the United States population) with a poor prognosis (Brooks, S. E., et al., Gynecol Oncol 93(1): 204-208 (2004)). It is well recognized that cancer is an enormous global health problem. The American Cancer Society estimates that in 2008 alone there were an estimated 12.7 million new diagnoses of cancer and 7.6 million deaths caused by cancer Reynolds, P. N., et al., Nat Biotech, 19(9): 838-842 (2001)). The time at which a cancer is detected, both at initial cancer diagnosis and during tumor recurrence, is one of the most important prognostic factors that substantially affect patient outcome, because if cancer is detected early, current treatments are likely to be more effective (Etzioni, R., et al., Nat Rev Cancer, 3(4): 243-252 (2003)).

Unfortunately, the majority of cancers are detected relatively late, leading to high mortality rates. These rates are expected to double by 2030 unless more effective detection strategies and treatments are developed. To stem the tremendous loss of life caused by this terrible disease, a broadly applicable tool capable of detecting cancers in their earliest stages is urgently needed. Proper differentiation between benign and malignant uterine lesions can dramatically improve the efficacy of patient treatment modalities. However, despite marvelous progress in cancer specific blood-based biomarkers, many of such biomarkers have failed clinically because of presence of limitations such as highly variable background expression from nonmalignant tissues and tumor heterogeneity.

Therefore, it is an object of the invention to provide compositions and methods for the early detection of cancer, in particular uterine cancer.

It is another object of the invention to provide compositions and methods for the treatment of cancer, in particular uterine cancer.

SUMMARY OF THE INVENTION

Compositions and methods for the detection and treatment of cancer are provided. It has been discovered that uterine cancer cells selectively induce the survivin promoter to express a gene product. One embodiment provides a method for detecting uterine malignancy by systemic administration of a cancer-specific vector that utilizes a survivin promoter to drive expression of a reporter gene. The expression of the reporter gene is detectable exclusively in malignant cells, for example using conventional imagining techniques.

Methods for treating uterine cancer are also provided. One method for treating uterine cancer includes administering to a subject suspected of having uterine cancer an expression vector encoding a cytotoxic agent, wherein expression of the cytotoxic agent is under the control of a survivin promoter. The vector can be administered systemically or directly into the uterus.

Another embodiment provides a uterine cell containing a viral vector, wherein the viral vector contains a survivin promoter. Preferred vectors are adenoviral vectors.

BRIEF DESCRIPTION OF THE DRAWINGS

FIG. 7A is shows images thirty minutes post injection. FIG. 7B shows images one hour post injection.

DETAILED DESCRIPTION OF THE INVENTION

I. Definitions

Figures 1A, 1B, 1C:
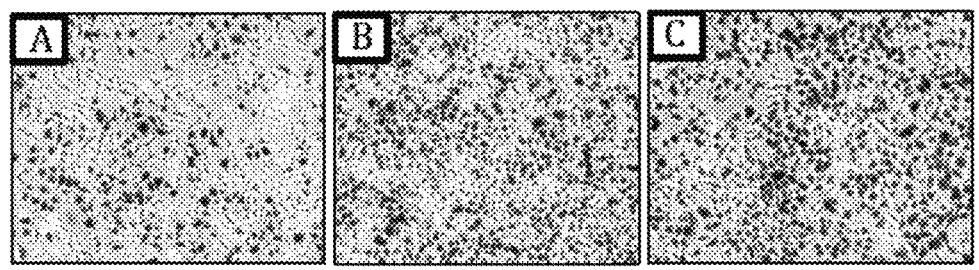
FIGS. 1A-1C are micrographs showing X-Gal staining of human SK-UT 1 cells after transfection with Ad-Lac Z reporter gene at multiplicity of infection 1 MOI (FIG. 1A), 3 MOI (FIG. 1B) and 5 MOI (FIG. 1C).

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "adenovirus" as used herein refers to a non-enveloped icosahedral double-stranded DNA virus having about a linear genome of about 36 kb.

The term "tumor-specific promoter" as used herein refers to a promoter which is activated specifically in a tumor cell compared to a normal cell to facilitate a transcription of a gene operably linked to the promoter.

The term "nucleic acid construct" or "nucleic acid cassette" as used herein refers to a nucleotide sequence constructed for insertion to an expression vector.

The term "vector" as used herein refers to a vehicle for gene transfer as that term is understood by those skilled in the art, and includes viruses, plasmids, and the like.

The term "operably linked" used herein refers to the arrangement of various nucleic acid molecule elements relative to each other such that the elements are functionally connected and are able to interact with each other.

The term "promoter" refers to a regulatory nucleic acid sequence, typically located upstream (5') of a gene or protein coding sequence that, in conjunction with various elements, is responsible for regulating the expression of the gene or protein coding sequence.

The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells can utilize promoters, polyadenylation signals, and enhancers.

II. Nucleic Acid Constructs

Nucleic acid constructs for detecting or treating uterine cancer include, but are not limited to expression vectors under the control of a Survivin promoter. For detecting cancer cells, the constructs include a reporter gene. Constructs for treating cancer encode a cytotoxic agent or oncolytic virus. Preferred constructs are viral vectors. The virus can be selected from the group consisting of adenovirus, adeno-associated virus, retrovirus, lentivirus, herpes simplex virus, and reovirus. Preferably, the virus is an adenovirus, and most preferably an adenovirus derived from primates. Adenoviruses infect both non-dividing and dividing cells unlike retroviruses and replicate as episomal elements in the nucleus without integrating with host genome, thereby not disrupting host genome. Adenoviruses are also useful for gene therapy due to high efficacy, long and safe storage, and low restriction in inserting an exogenous gene.

A. Constructs for Detecting Uterine Cancer

Constructs for detecting uterine cancer include but are not limited to the constructs reported in Zhu, Z., et al., Cancer Gene Therapy, 11:256-262 (2004) and Houdt, W., et al., J Neurosurg, 104:583-592 (2006) both of which are incorporated by reference in their entireties.

A preferred nucleic acid construct is a viral vector containing a reporter gene under the control of a survivin promoter. The reporter gene can encode an enzyme or a luminescent or fluorescent gene product. An exemplary fluorescent gene product is Green Fluorescent Protein. The reporter gene can encode luciferase which catalyzes a reaction with luciferin to produce light.

1. Preferred Survivin Promoter Sequences

A nucleic acid sequence for the human Survivin gene is (SEQ ID NO: 4)
```
  1  TCTAGACATG CGGATATATT CAAGCTGGGC ACAGCACAGC AGCCCCACCC CAGGCAGCTT

61  GAAATCAGAG CTGGGGTCCA AAGGGACCAC ACCCCGAGGG ACTGTGTGGG GGTCGGGGCA

121  CACAGGCCAC TGCTTCCCCC CGTCTTTCTC AGCCATTCCT GAAGTCAGCC TCACTCTGCT

181  TCTCAGGGAT TTCAAATGTG CAGAGACTCT GGCACTTTTG TAGAAGCCCC TTCTGGTCCT

241  AACTTACACC TGGATGCTGT GGGGCTGCAG CTGCTGCTCG GGCTCGGGAG GATGCTGGGG
```

-continued

```
 301  GCCCGGTGCC CATGAGCTTT TGAAGCTCCT GGAACTCGGT TTTGAGGGTG TTCAGGTCCA
 361  GGTGGACACC TGGGCTGTCC TTGTCCATGC ATTTGATGAC ATTGTGTGCA GAAGTGAAAA
 421  GGAGTTAGGC CGGGCATGCT GGCTTATGCC TGTAATCCCA GCACTTTGGG AGGCTGAGGC
 481  GGGTGGATCA CGAGGTCAGG AGTTCAATAC CAGCCTGGCC AAGATGGTGA AACCCCGTCT
 541  CTACTAAAAA TACAAAAAAA TTAGCCGGGC ATGGTGGCGG GCGCATGTAA TCCCAGCTAC
 601  TGGGGGGGCT GAGGCAGAGA ATTGCTGGAA CCCAGGAGAT GGAGGTTGCA GTGAGCCAAG
 661  ATTGTGCCAC TGCACTGCAC TCCAGCCTGG CGACAGAGCA AGACTCTGTC TCAAAAAAAA
 721  AAAAAAAAAG TGAAAAGGAG TTGTTCCTTT CCTCCCTCCT GAGGGCAGGC AACTGCTGCG
 781  GTTGCCAGTG GAGGTGGTGC GTCCTTGGTC TGTGCCTGGG GCCACCCCA GCAGAGGCCA
 841  TGGTGGTGCC AGGGCCCGGT TAGCGAGCCA ATCAGCAGGA CCCAGGGGCG ACCTGCCAAA
 901  GTCAACTGGA TTTGATAACT GCAGCGAAGT TAAGTTTCCT GATTTTGATG ATTGTGTTGT
 961  GGTTGTGTAA GAGAATGAAG TATTTCGGGG TAGTATGGTA ATGCCTTCAA CTTACAAACG
1021  GTTCAGGTAA ACCACCCATA TACATACATA TACATGCATG TGATATATAC ACATACAGGG
1081  ATGTGTGTGT GTTCACATAT ATGAGGGGAG AGAGACTAGG GGAGAGAAAG TAGGTTGGGG
1141  AGAGGGAGAG AGAAAGGAAA ACAGGAGACA GAGAGAGAGC GGGGAGTAGA GAGAGGGAAG
1201  GGGTAAGAGA GGGAGAGGAG GAGAGAAAGG GAGGAAGAAG CAGAGAGTGA ATGTTAAAGG
1261  AAACAGGCAA AACATAAACA GAAAATCTGG GTGAAGGGTA TATGAGTATT CTTTGTACTA
1321  TTCTTGCAAT TATCTTTTAT TTAAATTGAC ATCGGGCCGG GCGCAGTGGC TCACATCTGT
1381  AATCCCAGCA CTTTGGGAGG CCGAGGCAGG CAGATCACTT GAGGTCAGGA GTTTGAGACC
1441  AGCCTGGCAA ACATGGTGAA ACCCCATCTC TACTAAAAAT ACAAAAATTA GCCTGGTGTG
1501  GTGGTGCATG CCTTTAATCT CAGCTACTCG GGAGGCTGAG GCAGGAGAAT CGCTTGAACC
1561  CGTGGCGGGG AGGAGGTTGC AGTGAGCTGA GATCATGCCA CTGCACTCCA GCCTGGGCGA
1621  TAGAGCGAGA CTCAGTTTCA AATAAATAAA TAAACATCAA AATAAAAAGT TACTGTATTA
1681  AAGAATGGGG GCGGGGTGGG AGGGGTGGGG AGAGGTTGCA AAAATAAATA AATAAATAAA
1741  TAAACCCCAA AATGAAAAAG ACAGTGGAGG CACCAGGCCT GCGTGGGGCT GGAGGGCTAA
1801  TAAGGCCAGG CCTCTTATCT CTGGCCATAG AACCAGAGAA GTGAGTGGAT GTGATGCCCA
1861  GCTCCAGAAG TGACTCCAGA ACACCCTGTT CCAAAGCAGA GGACACACTG ATTTTTTTTT
1921  TAATAGGCTG CAGGACTTAC TGTTGGTGGG ACGCCCTGCT TTGCGAAGGG AAAGGAGGAG
1981  TTTGCCCTGA GCACAGGCCC CCACCCTCCA CTGGGCTTTC CCCAGCTCCC TTGTCTTCTT
2041  ATCACGGTAG TGGCCCAGTC CCTGGCCCCT GACTCCAGAA GGTGGCCCTC CTGGAAACCC
2101  AGGTCGTGCA GTCAACGATG TACTCGCCGG GACAGCGATG TCTGCTGCAC TCCATCCCTC
2161  CCCTGTTCAT TTGTCCTTCA TGCCCGTCTG GAGTAGATGC TTTTTGCAGA GGTGGCACCC
2221  TGTAAAGCTC TCCTGTCTGA CTTTTTTTTT TTTTTTAGAC TGAGTTTTGC TCTTGTTGCC
2281  TAGGCTGGAG TGCAATGGCA CAATCTCAGC TCACTGCACC CTCTGCCTCC CGGGTTCAAG
2341  CGATTCTCCT GCCTCAGCCT CCCGAGTAGT TGGGATTACA GGCATGCACC ACCACGCCCA
2401  GCTAATTTTT GTATTTTTAG TAGAGACAAG GTTTCACCGT GATGGCCAGG CTGGTCTTGA
2461  ACTCCAGGAC TCAAGTGATG CTCCTGCCTA GGCCTCTCAA AGTGTTGGGA TTACAGGCGT
2521  GAGCCACTGC ACCCGGCCTG CACGCGTTCT TTGAAAGCAG TCGAGGGGC GCTAGGTGTG
2581  GGCAGGGACG AGCTGGCGCG GCGTCGCTGG GTGCACCGCG ACCACGGGCA GAGCCACGCG
2641  GCGGGAGGAC TACAACTCCC GGCACACCCC GCGCCGCCCC GCCTCTACTC CCAGAAGGCC
```

-continued

```
2701 GCGGGGGGTG GACCGCCTAA GAGGGCGTGC GCTCCCGACA TGCCCCGCGG CGCGCCATTA
2761 ACCGCCAGAT TTGAATCGCG GGACCCGTTG GCAGAGGTGG CGGCGGCGGC ATGGGTGCCC
2821 CGACGTTGCC CCCTGCCTGG CAGCCCTTTC TCAAGGACCA CCGCATCTCT ACATTCAAGA
2881 ACTGGCCCTT CTTGGAGGGC TGCGCCTGCA CCCCGGAGCC GGTGAGACTG CCCGGCCTCC
2941 TGGGGTCCCC CACGCCCGCC TTGCCCTGTC CCTAGCGAGG CCACTGTGAC TGGGCCTCGG
3001 GGGTACAAGC CGCCCTCCCC TCCCCGTCCT GTCCCCAGCG AGGCCACTGT GGCTGGGCCC
3061 CTTGGGTCCA GGCCGGCCTC CCCTCCCTGC TTTGTCCCCA TCGAGGCCTT TGTGGCTGGG
3121 CCTCGGGGTT CCGGGCTGCC ACGTCCACTC ACGAGCTGTG CTGTCCCTTG CAGATGGCCG
3181 AGGCTGGCTT CATCCACTGC CCCACTGAGA ACGAGCCAGA CTTGGCCCAG TGTTTCTTCT
3241 GCTTCAAGGA GCTGGAAGGC TGGGAGCCAG ATGACGACCC CATGTAAGTC TTCTCTGGCC
3301 AGCCTCGATG GGCTTTGTTT TGAACTGAGT TGTCAAAAGA TTTGAGTTGC AAAGACACTT
3361 AGTATGGGAG GGTTGCTTTC CACCCTCATT GCTTCTTAAA CAGCTGTTGT GAACGGATAC
3421 CTCTCTATAT GCTGGTGCCT TGGTGATGCT ACAACCTAA TTAAATCTCA TTTGACCAAA
3481 ATGCCTTGGG GTGGACGTAA GATGCCTGAT GCCTTTCATG TTCAACAGAA TACATCAGCA
3541 GACCCTGTTG TTGTGAACTC CCAGGAATGT CCAAGTGCTT TTTTTGAGAT TTTTTAAAAA
3601 ACAGTTTAAT TGAAATATAA CCTACACAGC ACAAAAATTA CCCTTTGAAA GTGTGCACTT
3661 CACACTTTCG GAGGCTGAGG CGGGCGGATC ACCTGAGGTC AGGAGTTCAA GACCTGCCTG
3721 GCCAACTTGG CGAAACCCCG TCTCTACTAA AAATACAAAA ATTAGCCGGG CATGGTAGCG
3781 CACGCCCGTA ATCCCAGCTA CTCGGGAGGC TAAGGCAGGA GAATCGCTTG AACCTGGGAG
3841 GCGGAGGTTG CAGTGAGCCG AGATTGTGCC AATGCACTCC AGCCTCGGCG ACAGAGCGAG
3901 ACTCCGTCAT AAAAATAAAA AATTGAAAAA AAAAAAGAA AGAAAGCATA TACTTCAGTG
3961 TTGTTCTGGA TTTTTTTCTT CAAGATGCCT AGTTAATGAC AATGAAATTC TGTACTCGGA
4021 TGGTATCTGT CTTTCCACAC TGTAATGCCA TATTCTTTTC TCACCTTTTT TTCTGTCGGA
4081 TTCAGTTGCT TCCACAGCTT TAATTTTTTT CCCCTGGAGA ATCACCCCAG TTGTTTTTCT
4141 TTTTGGCCAG AAGAGAGTAG CTGTTTTTTT TCTTAGTATG TTTGCTATGG TGGTTATACT
4201 GCATCCCCGT AATCACTGGG AAAAGATCAG TGGTATTCTT CTTGAAAATG AATAAGTGTT
4261 ATGATATTTT CAGATTAGAG TTACAACTGG CTGTCTTTTT GGACTTTGTG TGGCCATGTT
4321 TTCATTGTAA TGCAGTTCTG GTAACGGTGA TAGTCAGTTA TACAGGGAGA CTCCCCTAGC
4381 AGAAAATGAG AGTGTGAGCT AGGGGGTCCC TTGGGGAACC CGGGGCAATA ATGCCCTTCT
4441 CTGCCCTTAA TCCTTACAGT GGGCCGGGCA CGGTGGCTTA CGCCTGTAAT ACCAGCACTT
4501 TGGGAGGCCG AGGCGGGCGG ATCACGAGGT CAGGAGATCG AGACCATCTT GGCTAATACG
4561 GTGAAACCCC GTCTCCACTA AAAATACAAA AAATTAGCCG GGCGTGGTGG TGGGCGCCTG
4621 TAGTCCCAGC TACTCGGGAG GCTGAGGCAG GAGAATGGCG TGAACCCAGG AGGCGGAGCT
4681 TGCAGTGAGC CGAGATTGCA CCACTGCACT CCAGCCTGGG CGACAGAATG AGACTCCGTC
4741 TCAAAAAAAA AAAAAAAGA AAAAAATCTT TACAGTGGAT TACATAACAA TTCCAGTGAA
4801 ATGAAATTAC TTCAAACAGT TCCTTGAGAA TGTTGGAGGG ATTTGACATG TAATTCCTTT
4861 GGACATATAC CATGTAACAC TTTTCCAACT AATTGCTAAG GAAGTCCAGA TAAAATAGAT
4921 ACATTAGCCA CACAGATGTG GGGGGAGATG TCCACAGGGA GAGAGAAGGT GCTAAGAGGT
4981 GCCATATGGG AATGTGGCTT GGGCAAAGCA CTGATGCCAT CAACTTCAGA CTTGACGTCT
5041 TACTCCTGAG GCAGAGCAGG GTGTGCCTGT GGAGGGCGTG GGGAGGTGGC CCGTGGGGAG
5101 TGGACTGCCG CTTTAATCCC TTCAGCTGCC TTTCCGCTGT TGTTTTGATT TTTCTAGAGA
```

-continued

```
5161  GGAACATAAA AAGCATTCGT CCGGTTGCGC TTTCCTTTCT GTCAAGAAGC AGTTTGAAGA

5221  ATTAACCCTT GGTGAATTTT TGAAACTGGA CAGAGAAAGA GCCAAGAACA AAATTGTATG

5281  TATTGGGAAT AAGAACTGCT CAAACCCTGT TCAATGTCTT TAGCACTAAA CTACCTAGTC

5341  CCTCAAAGGG ACTCTGTGTT TTCCTCAGGA AGCATTTTTT TTTTTTTCT GAGATAGAGT

5401  TTCACTCTTG TTGCCCAGGC TGGAGTGCAA TGGTGCAATC TTGGCTCACT GCAACCTCTG

5461  CCTCTCGGGT TCAAGTGATT CTCCTGCCTC AGCCTCCCAA GTAACTGGGA TTACAGGGAA

5521  GTGCCACCAC ACCCAGCTAA TTTTTGTATT TTTAGTAGAG ATGGGGTTTC ACCACATTGC

5581  CCAGGCTGGT CTTGAACTCC TGACCTCGTG ATTCGCCCAC CTTGGCCTCC CAAAGTGCTG

5641  GGATTACAGG CGTGAACCAC CACGCCTGGC TTTTTTTTTT TTGTTCTGAG ACACAGTTTC

5701  ACTCTGTTAC CCAGGCTGGA GTAGGTGGC CTGATCTCGG ATCACTGCAA CCTCCGCCTC

5761  CTGGGCTCAA GTGATTTGCC TGCTTCAGCC TCCCAAGTAG CCGAGATTAC AGGCATGTGC

5821  CACCACACCC AGGTAATTTT TGTATTTTTG GTAGAGACGA GGTTTCACCA TGTTGGCCAG

5881  GCTGGTTTTG AACTCCTGAC CTCAGGTGAT CCACCCGCCT CAGCCTCCCA AAGTGCTGAG

5941  ATTATAGGTG TGAGCCACCA CACCTGGCCT CAGGAAGTAT TTTTATTTTT AAATTTATTT

6001  ATTTATTTGA GATGGAGTCT TGCTCTGTCG CCCAGGCTAG AGTGCAGCGA CGGGATCTCG

6061  GCTCACTGCA AGCTCCGCCC CCCAGGTTCA AGCCATTCTC CTGCCTCAGC CTCCCGAGTA

6121  GCTGGGACTA CAGGCGCCCG CCACCACACC CGGCTAATTT TTTTGTATTT TTAGTAGAGA

6181  CGGGTTTTCA CCGTGTTAGC CAGGAGGGTC TTGATCTCCT GACCTCGTGA TCTGCCTGCC

6241  TCGGCCTCCC AAAGTGCTGG GATTACAGGT GTGAGCCACC ACACCCGGCT ATTTTTATTT

6301  TTTTGAGACA GGGACTCACT CTGTCACCTG GCTGCAGTG CAGTGGTACA CCATAGCTCA

6361  CTGCAGCCTC GAACTCCTGA GCTCAAGTGA TCCTCCCACC TCATCCTCAC AAGTAATTGG

6421  GACTACAGGT GCACCCCACC ATGCCCACCT AATTTATTTA TTTATTTATT TATTTATTTT

6481  CATAGAGATG AGGGTTCCCT GTGTTGTCCA GGCTGGTCTT GAACTCCTGA GCTCACGGGA

6541  TCCTTTTGCC TGGGCCTCCC AAAGTGCTGA GATTACAGGC ATGAGCCACC GTGCCCAGCT

6601  AGGAATCATT TTTAAAGCCC CTAGGATGTC TGTGTGATTT TAAAGCTCCT GGAGTGTGGC

6661  CGGTATAAGT ATATACCGGT ATAAGTAAAT CCCACATTTT GTGTCAGTAT TTACTAGAAA

6721  CTTAGTCATT TATCTGAAGT TGAAATGTAA CTGGGCTTTA TTTATTTATT TATTTATTTA

6781  TTTATTTTTA ATTTTTTTTT TTGAGACGAG TCTCACTTTG TCACCCAGGC TGGAGTGCAG

6841  TGGCACGATC TCGGCTCACT GCAACCTCTG CCTCCCGGGG TCAAGCGATT CTCCTGCCTT

6901  AGCCTCCCGA GTAGCTGGGA CTACAGGCAC GCACCACCAT GCCTGGCTAA TTTTTGTATT

6961  TTTAGTAGAC GGGGTTTCAC CATGCTGGCC AAGCTGGTCT CAAACTCCTG ACCTTGTGAT

7021  CTGCCCGCTT TAGCCTCCCA GAGTGCTGGG ATTACAGGCA TGAGCCACCA TGCGTGGTCT

7081  TTTTAAAATT TTTTGATTTT TTTTTTTTTT GAGACAGAGC CTTGCTCTGT CGCCCAGGCT

7141  GGAGTGCAGT GGCACGATCT CAGCTCACTA CAAGCTCCGC CTCCCGGGTT CACGCCATTC

7201  TTCTGCCTCA GCCTCCTGAG TAGCTGGGAC TACAGGTGCC CACCACCACG CCTGGCTAAT

7261  TTTTTTTGGT ATTTTTATTA GAGACAAGGT TTCATCATGT TGGCCAGGCT GGTCTCAAAC

7321  TCCTGACCTC AAGTGATCTG CCTGCCTCGG CCTCCCAAAG CGCTGAGATT ACAGGTGTGA

7381  TCTACTGCGC CAGGCCTGGG CGTCATATAT TCTTATTTGC TAAGTCTGGC AGCCCCACAC

7441  AGAATAAGTA CTGGGGGATT CCATATCCTT GTAGCAAAGC CCTGGGTGGA GAGTCAGGAG

7501  ATGTTGTAGT TCTGTCTCTG CCACTTGCAG ACTTTGAGTT TAAGCCAGTC GTGCTCATGC
```

```
                    -continued
7561  TTTCCTTGCT AAATAGAGGT TAGACCCCCT ATCCATGGTT TTCTCAGGTT GCTTTTCAGC

7621  TTGAAAATTG TATTCCTTTG TAGAGATCAG CGTAAAATAA TTCTGTCCTT ATATGTGGCT

7681  TTATTTTAAT TTGAGACAGA GTGTCACTCA GTCGCCCAGG CTGGAGTGTG GTGGTGCGAT

7741  CTTGGCTCAC TGCGACCTCC ACCTCCCAGG TTCAAGCGAT TCTCGTGCCT CAGGCTCCCA

7801  AGTAGCTGAG ATTATAGGTG TGTGCCACCA GGCCCAGCTA ACTTTTGTAT TTTTAGTAGA

7861  GACAGGGTTT TGCCATGTTG GCTAAGCTGG TCTCGAACTC CTGGCCTCAA GTGATCTGCC

7921  CGCCTTGGCA TCCCAAAGTG CTGGGATTAC AGGTGTGAAC CACCACACCT GGCCTCAATA

7981  TAGTGGCTTT TAAGTGCTAA GGACTGAGAT TGTGTTTTGT CAGGAAGAGG CCAGTTGTGG

8041  GTGAAGCATG CTGTGAGAGA GCTTGTCACC TGGTTGAGGT TGTGGGAGCT GCAGCGTGGG

8101  AACTGGAAAG TGGGCTGGGG ATCATCTTTT TCCAGGTCAG GGGTCAGCCA GCTTTTCTGC

8161  AGCGTGCCAT AGACCATCTC TTAGCCCTCG TGGGTCAGAG TCTCTGTTGC ATATTGTCTT

8221  TTGTTGTTTT TCACAACCTT TTAGAAACAT AAAAAGCATT CTTAGCCCGT GGGCTGGACA

8281  AAAAAAGGCC ATGACGGGCT GTATGGATTT GGCCCAGCAG GCCCTTGCTT GCCAAGCCCT

8341  GTTTTAGACA AGGAGCAGCT TGTGTGCCTG AACCATCAT GGGCACAGGG GAGGAGCAGA

8401  GTGGATGTGG AGGTGTGAGC TGGAAACCAG GTCCCAGAGC GCTGAGAAAG ACAGAGGGTT

8461  TTTGCCCTTG CAAGTAGAGC AACTGAAATC TGACACCATC CAGTTCCAGA AAGCCCTGAA

8521  GTGCTGGTGG ACGCTGCGGG GTGCTCCGCT CTAGGGTTAC AGGGATGAAG ATGCAGTCTG

8581  GTAGGGGGAG TCCACTCACC TGTTGGAAGA TGTGATTAAG AAAAGTAGAC TTTCAGGGCC

8641  GGGCATGGTG GCTCACGCCT GTAATCCCAG CACTTTGGGA GGCCGAGGCG GGTGGATCAC

8701  GAGGTCAGGA GATCGAGACC ATCCTGGCTA ACATGGTGAA ACCCCGTCTT TACTAAAAAT

8761  ACAAAAAATT AGCTGGGCGT GGTGGCGGGC GCCTGTAGTC CCAGCTACTC GGGAGGCTGA

8821  GGCAGGAGAA TGGCGTGAAC CTGGGAGGTG GAGCTTGCTG TGAGCCGAGA TCGCGCCACT

8881  GCACTCCAGC CTGGGCGACA GAGCGAGACT CCGTCTCAAA AAAAAAAAA AAAGTAGGCT

8941  TTCATGATGT GTGAGCTGAA GGCGCAGTAG GCAGAAGTAG AGGCCTCAGT CCCTGCAGGA

9001  GACCCCTCGG TCTCTATCTC CTGATAGTCA GACCCAGCCA CACTGGAAAG AGGGGAGACA

9061  TTACAGCCTG CGAGAAAAGT AGGGAGATTT AAAAACTGCT TGGCTTTTAT TTTGAACTGT

9121  TTTTTTTGTT TGTTTGTTTT CCCCAATTCA GAATACAGAA TACTTTTATG GATTTGTTTT

9181  TATTACTTTA ATTTTGAAAC AATATAATCT TTTTTTTGTT GTTTTTTGA GACAGGGTCT

9241  TACTCTGTCA CCCAGGCTGA GTGCAGTGGT GTGATCTTGG CTCACCTCAG CCTCGACCCC

9301  CTGGGCTCAA ATGATTCTCC CACCTCAGCT TCCCAAGTAG CTGGGACCAC AGGTGCGTGT

9361  GTTGCGCTAT ACAAATCCTG AAGACAAGGA TGCTGTTGCT GGTGATGCTG GGGATTCCCA

9421  AGATCCCAGA TTTGATGGCA GGATGCCCCT GTCTGCTGCC TTGCCAGGGT GCCAGGAGGG

9481  CGCTGCTGTG GAAGCTGAGG CCCGGCCATC CAGGGCGATG CATTGGGCGC TGATTCTTGT

9541  TCCTGCTGCT GCCTCGGTGC TTAGCTTTTG AAACAATGAA ATAAATTAGA ACCAGTGTGA

9601  AAATCGATCA GGGAATAAAT TTAATGTGGA AATAAACTGA ACAACTAGT TCTTCATAAG

9661  AGTTTACTTG GTAAATACTT GTGATGAGGA CAAAACGAAG CACTAGAAGG AGAGGCGAGT

9721  TGTAGACCTG GGTGGCAGGA GTGTTTTGTT TGTTTTCTTT GGCAGGGTCT TGCTCTGTTG

9781  CTCAGGCTGG AGTACAGTGG CACAATCACA GCTCACTATA GCCTCGACCT CCTGGACTCA

9841  AGCAATCCTC CTGCCTCAGC CTCCCAGTAG CTGGGACTAC AGGCGCATGC CACCATGCCT

9901  GGCTAATTTT AAATTTTTTT TTTTCTCTTT TTTGAGATGG AATCTCACTC TGTCGCCCAG

9961  GCTGGAGTGC AGTGGCGTGA TCTCGGCTGA CGGCAAGCTC CGCCTCCCAG GTTCACTCCA
```

-continued

```
10021  TTCGCCTGCC TCAGCCTCCC AAGTAGCTGG GACTACAGGC GCTGGGATTA CAAACCCAAA
10081  CCCAAAGTGC TGGGATTACA GGCGTGAGCC ACTGCACCCG GCCTGTTTTG TCTTTCAATA
10141  GCAAGAGTTG TGTTTGCTTC GCCCCTACCT TTAGTGGAAA AATGTATAAA ATGGAGATAT
10201  TGACCTCCAC ATTGGGTGG TTAAATTATA GCATGTATGC AAAGGAGCTT CGCTAATTTA
10261  AGGCTTTTTT GAAAGAGAAG AAACTGAATA ATCCATGTGT GTATATATAT TTTAAAAGCC
10321  ATGGTCATCT TTCCATATCA GTAAAGCTGA GGCTCCCTGG GACTGCAGAG TTGTCCATCA
10381  CAGTCCATTA TAAGTGCGCT GCTGGGCCAG GTGCAGTGGC TTGTGCCTGA ATCCCAGCAC
10441  TTTGGGAGGC CAAGGCAGGA GGATTCATTG AGCCCAGGAG TTTTGAGGCG AGCCTGGGCA
10501  ATGTGGCCAG ACCTCATCTC TTCAAAAAAT ACACAAAAAA TTAGCCAGGC ATGGTGGCAC
10561  GTGCCTGTAG TCTCAGCTAC TCAGGAGGCT GAGGTGGGAG GATCACTTTG AGCCTTGCAG
10621  GTCAAAGCTG CAGTAAGCCA TGATCTTGCC ACTGCATTCC AGCCTGGATG ACAGAGCGAG
10681  ACCCTGTCTC TAAAAAAAAA AAAACCCAAA CGGTGCACTG TTTTCTTTTT TCTTATCAAT
10741  TTATTATTTT TAAATTAAAT TTTCTTTTAA TAATTTATAA ATTATAAATT TATATTAAAA
10801  AATGACAAAT TTTTATTACT TATACATGAG GTAAAACTTA GGATATATAA AGTACATATT
10861  GAAAAGTAAT TTTTTGGCTG GCACAGTGGC TCACACCTGT AATCCCAGCA CTTTGGGAGG
10921  CCGTGGCGGG CAGATCACAT GAGATCATGA GTTCGAGACC AACCTGACCA ACATGGAGAG
10981  ACCCCATCTC TACTAAAAAT ACAAAATTAG CCGGGGTGGT GGCGCATGCC TGTAATCCCA
11041  GCTACTCGGG AGGCTGAGGC AGGAGAATCT CTTGAACCCG GGAGGCAGAG GTTGCGGTGA
11101  GCCAAGATCG TGCCTTTGCA CACCAGCCTA GGCAACAAGA GCGAAAGTCC GTCTCAAAAA
11161  AAAAGTAATT TTTTTTAAGT TAACCTCTGT CAGCAAACAA ATTTAACCCA ATAAAGGTCT
11221  TTGTTTTTTA ATGTAGTAGA GGAGTTAGGG TTTATAAAAA ATATGGTAGG GAAGGGGGTC
11281  CCTGGATTTG CTAATGTGAT TGTCATTTGC CCCTTAGGAG AGAGCTCTGT TAGCAGAATG
11341  AAAAAATTGG AAGCCAGATT CAGGGAGGGA CTGGAAGCAA AAGAATTTCT GTTCGAGGAA
11401  GAGCCTGATG TTTGCCAGGG TCTGTTTAAC TGGACATGAA GAGGAAGGCT CTGGACTTTC
11461  CTCCAGGAGT TTCAGGAGAA AGGTAGGGCA GTGGTTAAGA GCAGAGCTCT GCCTAGACTA
11521  GCTGGGGTGC CTAGACTAGC TGGGGTGCCC AGACTAGCTG GGGTGCCTAG ACTAGCTGGG
11581  TACTTTGAGT GGCTCCTTCA GCCTGGACCT CGGTTTCCTC ACCTGTATAG TAGAGATATG
11641  GGAGCACCCA GCGCAGGATC ACTGTGAACA TAAATCAGTT AATGGAGGAA GCAGGTAGAG
11701  TGGTGCTGGG TGCATACCAA GCACTCCGTC AGTGTTTCCT GTTATTCGAT GATTAGGAGG
11761  CAGCTTAAAC TAGAGGGAGT TGAGCTGAAT CAGGATGTTT GTCCCAGGTA GCTGGGAATC
11821  TGCCTAGCCC AGTGCCCAGT TTATTTAGGT GCTCTCTCAG TGTTCCCTGA TTGTTTTTTC
11881  CTTTGTCATC TTATCTACAG GATGTGACTG GAAGCTCTG GTTTCAGTGT CATGTGTCTA
11941  TTCTTTATTT CCAGGCAAAG GAAACCAACA ATAAGAAGAA AGAATTTGAG GAAACTGCGA
12001  AGAAAGTGCG CCGTGCCATC GAGCAGCTGG CTGCCATGGA TTGAGGCCTC TGGCCGGAGC
12061  TGCCTGGTCC CAGAGTGGCT GCACCACTTC CAGGGTTTAT TCCCTGGTGC CACCAGCCTT
12121  CCTGTGGGCC CCTTAGCAAT GTCTTAGGAA AGGAGATCAA CATTTTCAAA TTAGATGTTT
12181  CAACTGTGCT CCTGTTTTGT CTTGAAAGTG GCACCAGAGG TGCTTCTGCC TGTGCAGCGG
12241  GTGCTGCTGG TAACAGTGGC TGCTTCTCTC TCTCTCTCTC TTTTTTGGGG GCTCATTTTT
12301  GCTGTTTTGA TTCCCGGGCT TACCAGGTGA GAAGTGAGGG AGGAAGAAGG CAGTGTCCCT
12361  TTTGCTAGAG CTGACAGCTT TGTTCGCGTG GGCAGAGCCT TCCACAGTGA ATGTGTCTGG
```

-continued

```
12421 ACCTCATGTT GTTGAGGCTG TCACAGTCCT GAGTGTGGAC TTGGCAGGTG CCTGTTGAAT

12481 CTGAGCTGCA GGTTCCTTAT CTGTCACACC TGTGCCTCCT CAGAGGACAG TTTTTTTGTT

12541 GTTGTGTTTT TTTGTTTTTT TTTTTTGGTA GATGCATGAC TTGTGTGTGA TGAGAGAATG

12601 GAGACAGAGT CCCTGGCTCC TCTACTGTTT AACAACATGG CTTTCTTATT TTGTTTGAAT

12661 TGTTAATTCA CAGAATAGCA CAAACTACAA TTAAAACTAA GCACAAAGCC ATTCTAAGTC

12721 ATTGGGGAAA CGGGGTGAAC TTCAGGTGGA TGAGGAGACA GAATAGAGTG ATAGGAAGCG

12781 TCTGGCAGAT ACTCCTTTTG CCACTGCTGT GTGATTAGAC AGGCCCAGTG AGCCGCGGGG

12841 CACATGCTGG CCGCTCCTCC CTCAGAAAAA GGCAGTGGCC TAAATCCTTT TTAAATGACT

12901 TGGCTCGATG CTGTGGGGGA CTGGCTGGGC TGCTGCAGGC CGTGTGTCTG TCAGCCCAAC

12961 CTTCACATCT GTCACGTTCT CCACACGGGG GAGAGACGCA GTCCGCCCAG GTCCCCGCTT

13021 TCTTTGGAGG CAGCAGCTCC CGCAGGGCTG AAGTCTGGCG TAAGATGATG GATTTGATTC

13081 GCCCTCCTCC CTGTCATAGA GCTGCAGGGT GGATTGTTAC AGCTTCGCTG GAAACCTCTG

13141 GAGGTCATCT CGGCTGTTCC TGAGAAATAA AAAGCCTGTC ATTTCAAACA CTGCTGTGGA

13201 CCCTACTGGG TTTTTAAAAT ATTGTCAGTT TTTCATCGTC GTCCCTAGCC TGCCAACAGC

13261 CATCTGCCCA GACAGCCGCA GTGAGGATGA GCGTCCTGGC AGAGACGCAG TTGTCTCTGG

13321 GCGCTTGCCA GAGCCACGAA CCCCAGACCT GTTTGTATCA TCCGGGCTCC TTCCGGGCAG

13381 AAACAACTGA AAATGCACTT CAGACCCACT TATTTATGCC ACATCTGAGT CGGCCTGAGA

13441 TAGACTTTTC CCTCTAAACT GGGAGAATAT CACAGTGGTT TTTGTTAGCA GAAATGCAC

13501 TCCAGCCTCT GTACTCATCT AAGCTGCTTA TTTTTGATAT TTGTGTCAGT CTGTAAATGG

13561 ATACTTCACT TTAATAACTG TTGCTTAGTA ATTGGCTTTG TAGAGAAGCT GGAAAAAAAT

13621 GGTTTTGTCT TCAACTCCTT TGCATGCCAG GCGGTGATGT GGATCTCGGC TTCTGTGAGC

13681 CTGTGCTGTG GGCAGGGCTG AGCTGGAGCC GCCCCTCTCA GCCCGCCTGC CACGGCCTTT

13741 CCTTAAAGGC CATCCTTAAA ACCAGACCCT CATGGCTGCC AGCACCTGAA AGCTTCCTCG

13801 ACATCTGTTA ATAAAGCCGT AGGCCCTTGT CTAAGCGCAA CCGCCTAGAC TTTCTTTCAG

13861 ATACATGTCC ACATGTCCAT TTTTCAGGTT CTCTAAGTTG GAGTGGAGTC TGGGAAGGGT

13921 TGTGAATGAG GCTTCTGGGC TATGGGTGAG GTTCCAATGG CAGGTTAGAG CCCCTCGGGC

13981 CAACTGCCAT CCTGGAAAGT AGAGACAGCA GTGCCCGCTG CCCAGAAGAG ACCAGCAAGC

14041 CAAACTGGAG CCCCCATTGC AGGCTGTCGC CATGTGGAAA GAGTAACTCA CAATTGCCAA

14101 TAAAGTCTCA TGTGGTTTTA TCTACTTTTT TTTTCTTTTT CTTTTTTTTT GAGACAAGGC

14161 CTTGCCCTCC CAGGCTGGAG TGCAGTGGAA TGACCACAGC TCACCGCAAC CTCAAATTCT

14221 TGCGTTCAAG TGAACCTCCC ACTTTAGCCT CCCAAGTAGC TGGGACTACA GGCGCACGCC

14281 ATCACACCCG GCTAATTGAA AAATTTTTTT TTTGTTTAG ATGGAATCTC ACTTTGTTGC

14341 CCAGGCTGGT CTCAAACTCC TGGGCTCAAG TGATCATCCT GCTTCAGCGT CCGACTTGTT

14401 GGTATTATAG GCGTGAGCCA CTGGGCCTGA CCTAGCTACC ATTTTTTAAT GCAGAAATGA

14461 AGACTTGTAG AAATGAAATA ACTTGTCCAG GATAGTCGAA TAAGTAACTT TTAGAGCTGG

14521 GATTTGAACC CAGGCAATCT GGCTCCAGAG CTGGGCCCTC ACTGCTGAAG GACACTGTCA

14581 GCTTGGGAGG GTGGCTATGG TCGGCTGTCT GATTCTAGGG AGTGAGGGCT GTCTTTAAAG

14641 CACCCCATTC CATTTTCAGA CAGCTTTGTC AGAAAGGCTG TCATATGGAG CTGACACCTG

14701 CCTCCCCAAG GCTTCCATAG ATCCTCTCTG TACATTGTAA CCTTTTATTT TGAAATGAAA

14761 ATTCACAGGA AGTTGTAAGG CTAGTACAGG GGATCC.
```

The "ATG" start codon is underlined and bolded in the sequence above. See also GenBank Accession No. GenBank: U75285.1, Version: U75285.1 GI:2315862, *Homo sapiens apoptosis inhibitor survivin gene, complete cds*, and Ambrosini, et al., *Nature Medicine*, 3:917-921 (1997), each of which is specifically incorporated by reference herein in its entirety.

Figures 9, 10:
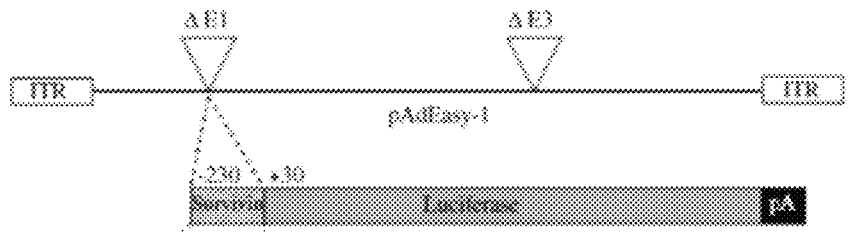
FIG. 9 is a DNA sequence analysis of the 5' flanking region of the human survivin gene (SEQ ID NO:1), including the ATG start codon and sequence up and downstream thereof (adapted from Li and Altieri, et al., *Biochem. J*, 344:305-311 (1999)). The amino acid sequence for the first exon of survivin is also shown (SEQ ID NO:3). Numbering is from the initiating ATG. Canonical Sp1, Sp1-like sites and CDE/CHR elements are boxed. Arrows indicate the position of the two main transcription start sites identified by primer extension and S1 nuclease protection experiments. An upward arrow indicates the first intron-exon boundary
FIG. 10 is a diagram (adapted from Zhu, et al., *Cancer Gene Therapy*, 11:256-262 (2004)) of an exemplary adenoviral vector including a survivin promoter driving expression of a lunciferase reporter open reading frame and a polyA tail cloned into the deleted E1 of an adenoviral vector backbone (pAdEasy-1). In this example, E3 is also deleted from the adenoviral vector backbone.

As illustrated in FIG. 9, for reference purposes, in addition to the nucleotide numbering provided herein and in the sequence listing, nucleotides beginning with, and downstream of, the "A" in a start codon can be referred to by counting positively from +1, while sequences upstream of "A" in the start codon can be referred to by counting negatively in the reverse direction from −1 beginning with the nucleotide immediately adjacent to and upstream of the start codon "A." Thus, in the sequence above, the underlined "ATG" can be referred to as nucleotides +1, +2, +3, respectively, while the "C" adjacent to and upstream of the "ATG," can be referred to as nucleotide −1.

The disclosed constructs for use in detection and treatment of uterine cancer typically include a survivin promoter. For example, the survivin promoter can include the expression control sequence of the nucleic acid sequence of SEQ ID NO:4, or SEQ ID NO:1, illustrated in FIG. 9, adapted from Li and Altieri, et al., *Biochem. J*, 344:305-311 (1999), which is specifically incorporated by reference in its entirety.

```
                                                               (SEQ ID NO: 1)
   1    AAATTGACAT CGGGCCGGGC GCAGTGGCTC ACATCTGTAA TCCCAGCACT TGGGAGGCC

61    GAGGCAGGCA GATCACTTGA GGTCAGGAGT TTGAGACCAG CCTGGCAAAC ATGGTGAAAC

121    CCCATCTCTA CTAAAAATAC AAAAATTAGC CTGGTGTGGT GGTGCATGCC TTTAATCTCA

181    GCTACTCGGG AGGCTGAGGC AGGAGAATCG CTTGAACCCG TGGCGGGGAG GAGGTTGCAG

241    TGAGCTGAGA TCATGCCACT GCACTCCAGC CTGGGCGATA GAGCGAGACT CAGTTTCAAA

301    TAAATAAATA AACATCAAAA TAAAAAGTTA CTGTATTAAA GAATGGGGGC GGGGTGGGAG

361    GGGTGGGGAG AGGTTGCAAA AATAAATAAA TAAATAAATA AACCCCAAAA TGAAAAAGAC

421    AGTGGAGGCA CCAGGCCTGC GTGGGGCTGG AGGGCTAATA AGGCaAGGCC TCTTATCTCT

481    GGCCATAGAA CCAGAGAAGT GAGTGGATGT GATGCCCAGC TCCAGAAGTG ACTCCAGAAC

541    ACCCTGTTCC AAAGCAGAGG ACACACTGAT TTTTTTTTTA ATAGGCTGCA GGAUTTACTG

601    TTGGTGGGAC GCCCTGCTTT GCGAAGGGAA AGGAGGAGTT TGCCCTGAGC ACAGGCCCCC

661    ACCCTCCACT GGGCTTTCCC CAGCTCCCTT GTCTTCTTAT CACGGTAGTG GCCCAGTCCC

721    TGGCCCCTGA CTCCAGAAGG TGGCCCTCCT GGAAACCCAG GTCGTGCAGT CAACGATGTA

781    CTCGCCGGGA CAGCGATGTC TGCTGCACTC CATCCCTCCC CTGTTCATTT GTCCTTCATG

841    CCCGTCTGGA GTAGATGCTT TTTGCAGAGG TGGCACCCTG TAAAGCTCTC CTGTCTGACT

901    TTTTTTTTTT TTTTAGACTG AGTTTTGCTC TTGTTGCCTA GGCTGGAGTG CAATGGCACA

961    ATCTCAGCTC ACTGCACCCT CTGCCTCCCG GGTTCAAGCG ATTCTCCTGC CTCAGCCTCC

1021    CGAGTAGTTG GGATTACAGG CATGCACCAC CACGCCCAGC TAATTTTTGT ATTTTTAGTA

1061    GAGACAAGGT TTCACCGTGA TGGCCAGGCT GGTCTTGAAC TCCAGGACTC AAGTGATGCT

1141    CCTGCCTAGG CCTCTCAAAG TGTTGGGATT ACAGGCGTGA GCCACTGCAC CCGGCCTGCA

1201    CGCGTTCTTT GAAAGCAGTC GAGGGGGCGC TAGGTGTGGG CAGGGACGAG CTGGCGCGGC

1261    GTCGCTGGGT GCACCGCGAC CACGGGCAGA GCCACGCGGC GGGAGGACTA CAACTCCCGG

1321    CACACCCCGC GCCGCCCCGC CTCTACTCCC AGAAGGCCGC GGGGGGTGGA CCGCCTAAGA

1361    GGGCGTGCGC TCCCGACATG CCCCGCGGCG CGCCATTAAC CGCCAGATTT GAATCGCGGG

1441    ACCCGTTGGC AGAGGTGGCG GCGGCGGCAT GGGTGCCCCG ACGTTGCCCC CTGCCTGGCA

1501    GCCCTTTCTC AAGGACCACC GCATCTCTAC ATTCAAGAAC TGGCCCTTCT TGGAGGGCTG

1561    CGCCTGCACC CCGGAGCGGG TGAGACTGCC CGGCC.
```

The "ATG" start codon is underlined and bolded in the sequence above.

In some embodiments, the survivin promoter includes a 260 by DNA fragment of the human survivin promoter according to nucleotides −230 to +30 of FIG. 9 (SEQ ID NO:1), or an expression controlling fragment thereof. Nucleotides −230 to +30 of FIG. 9 (SEQ ID NO:1) are:

```
                                                              (SEQ ID NO: 5)
  1   GGCAGGGACG AGCTGGCGCG GCGTCGCTGG GTGCACCGCG ACCACGGGCA GAGCCACGCG

61   GCGGGAGGAC TACAACTCCC GGCACACCCC GCGCCGCCCC GCCTCTACTC CCAGAAGGCC

121   GCGGGGGGTG GACCGCCTAA GAGGGCGTGC GCTCCCGACA TGCCCCGCGG CGCGCCATTA

181   ACCGCCAGAT TTGAATCGCG GGACCCGTTG GCAGAGGTGG CGGCGGCGGC ATGGGTGCCC

241   CGACGTTGCC CCCTGCCTGG.
```

The "ATG" start codon is underlined and bolded in the sequence above. In some embodiments, the expression controlling fragment includes nucleotides −230 to −1 of FIG. 9 (SEQ ID NO:1), which are:

```
                                                              (SEQ ID NO: 6)
  1    GGCAGGGACG AGCTGGCGCG GCGTCGCTGG GTGCACCGCG ACCACGGGCA GAGCCACGCG

61    GCGGGAGGAC TACAACTCCC GGCACACCCC GCGCCGCCCC GCCTCTACTC CCAGAAGGCC

121    GCGGGGGGTG GACCGCCTAA GAGGGCGTGC GCTCCCGACA TGCCCCGCGG CGCGCCATTA

181    ACCGCCAGAT TTGAATCGCG GGACCCGTTG GCAGAGGTGG CGGCGGCGGC.
```

In some embodiments, the survivin promoter is derived from a homologue or orthologue of the promoter of SEQ ID NO:1 or 4. The survivin promoter can be an expression controlling nucleic acid sequence having at least 60, 70, 80, 85, 90, 95, 96, 97, 98, or 99 percent sequence identity to the promoter of SEQ ID NO:1, or to a functional fragment thereof, such as nucleotides −230 to +30 of FIG. 9 (SEQ ID NO:1), which is SEQ ID NO:5, or −230 to −1 of FIG. 9 (SEQ ID NO:1), which is SEQ ID NO:6.

2. Preferred Reporters Genes

The disclosed constructs for detection of uterine cancer typically include a survivin promoter operably linked to a report. Suitable reporters are well known in the art, and include, but are not limited to, bacterial GUS gene, the firefly luciferase gene, and the cyan, green, red, and yellow fluorescent protein genes. These examples, are non-limiting, as the reporter can be any gene for which an easy and reliable assay is available can serve as the reporter gene. One of skill in the art knows which reporters are suitable or preferred for in vivo applications, ex vivo applications, or both.

In a particular embodiment, the reporter gene is luciferase gene of pGL3/Basic (Promega, catalog number E1751), GenBank accession no. U47295.2 (Cloning vector pGL3-Basic, complete sequence), which is specifically incorporated by reference in its entirety and provides the luciferase polypeptide sequence:

```
                                                              (SEQ ID NO: 2)
MEDAKNIKKGPAPFYPLEDGTAGEQLHKAMKRYALVPGTIAFTDAHIEVD

ITYAEYFEMSVRLAEAMKRYGLNTNHRIVVCSENSLQFFMPVLGALFIGV

AVAPANDIYNERELLNSMGISQPTVVEVSKKGLQKILNVQKKLPIIQKII

IMDSKTDYQGFQSMYTFVTSHLPPGFNEYDFVPESFDRDKTIALIMNSSG

STGLPKGVALPHRTACVRFSHARDPIFGNQIIPDTAILSVVPFHHGEGME

TTLGYLICGFRVVLMYRFEEELFLRSLQDYKIQSALLVPTLFSFFAKSTL

IDKYDLSNLHEIASGGAPLSKEVGEAVAKRFHLPGIRQGYGLTETTSAIL

ITPEGDDKPGAVGKVVPFFEAKVVDLDTGKTLGVNQRGELCVRGPMIMSG
```

-continued
```
YVNNPEATNALIDKDGWLHSGDIAYWDEDEHFFIVDRLKSLIKYKGYQVA

PAELESILLQHPNIFDAGVAGLPDDDAGELPAAVVVLEHGKTMTEKEIVD

YVASQVITAKKLRGGVVEVDEVPKGLTGKLDARKIREILIKAKKGGKIAV.
```

Accordingly, in some embodiments the reporter gene includes a nucleic acid sequence encoding SEQ ID NO:2, for example, the nucleic acid sequence including nucleotides 88-1740 of GenBank accession no. U47295.2.

3. Vectors

The disclosed constructs including a survivin promoter can be inserted, using known methods, into any suitable expression vector. In particular preferred embodiments, the vector is recombinant adenoviral vector. Suitable adenoviral vectors and methods of cloning expression constructs into them are known in the art.

In a particular embodiment, the vector is a human Ad5 adenovirus. Sequences for Ad5 are known in the art, and can be used as the backbone for survivin driven reporter constructs disclosed herein. See, for example, Genbank accession number M73260.1 (Mastadenovirus h5 gene, complete genome), which is specifically incorporated by reference herein in its entirety. In some embodiments, E1, E3, or both are deleted or substituted (He, et al., *Proc Natl Acad Sci USA.*, 95(5):2509-14 (1998)). For example, in some embodiments, an E1 deletion is a deletion of nucleotides 455-3512, or a fragment thereof. In some embodiments, an E3 deletion is a deletion of 28587-30464, or a fragment thereof.

4. Method of Making Constructs and Exemplary Constructs

Recombinant vectors that express a reporter operably linked to a survivin expression control sequence can be constructed according to methods that are known in the art. For example, in some embodiments, the vector includes a nucleic acid sequence encoding a survivin promoter operably linked to a nucleic acid sequence encoding a firefly luciferase open reading frame. The vector can be an adenoviral vector prepared according to known materials and methods. See, for example, the AdEasy system (Agilent Technologies, Quantum, etc.) and He, et al., *Proc Natl Acad Sci U.S.A.*, 95(5):2509-14 (1998). In a specific embodiment, a construct including a luciferase reporter gene from pGL3Basic and a simian virus 40 polyadenylation (SV40 poly-A) signal driven by a survivin promoter, are cloned into the E1-deleted region of the adenoviral vector backbone using the AdEasy system. The survivin promoter is a 260 by DNA fragment of the survivin promoter (nucleotides −230 to +30 according to Li and Altieri, et al., *Biochem. J,* 344:305-311 (1999)

In particular embodiments, the survivin promoter is PCR amplified with or without 5' and 3' ends containing restriction sites suitable for cloning, or the fragment is excised by restriction digestion from a plasmid containing the promoter. For example, BamHI/Hind III can be used to recover the 260 by sequence from pLuc-cycl.2 (Li and Altieri, et al., *Biochem. J,* 344:305-311 (1999), which is specifically incorporated by reference herein in its entirety). The promotor can optionally be subcloned into an intermediate vector, such as PBS IISK(+) vector (Stratagene, La Jolla, Calif.), for example to utilize alternative restriction sites, or to add or subtract other expression construct elements if-needed. For example, following subcloning of BamHI/Hind III fragment of pLuc-cycl.2, a SacI/HindIII fragment can be cloned into pGL3/Basic (Promega, catalog number E1751) to a construct with a survivin promoter operably linked to a luciferase open reading frame.

It will be appreciated that the foregoing is an exemplary preparation, and steps can be omitted, substituted, or added as is known in the art. For example, any of the subcloning steps can include PCR application of the desired fragment; alternative vectors can be utilized for an alternative luciferase sequences; an alternative reporter gene can be substituted for luciferase; the survivin promoter can include more or fewer nucleotides or can be an alternative promoter sequence compared to the 260 bp promoter sequence of pLuc-cycl.2 (e.g., having one or more polymorphisms, etc.); and/or other eukaryotic expression regulatory elements can be added or subtracted.

Once the expression construct is a prepared, it can be inserted into an adenoviral expression system. In some embodiments, the construct is subcloned into shuttle vector (e.g., pShuttle vector (Quantum, Montreal, Quebec, Canada)), and cloned into adenoviral expression system by homologous recombination, though alternative methods of preparing adenoviral vectors well known and can be substituted. In the specific embodiment described above, a KpnI/SalI fragment from pGL3B Survivin can be subcloned into pShuttle vector to create pShuttleGL3BSurvivin and homologous recombination can be performed in BJ5183 cells in accordance with the AdEasy System to create a recombinant adenovirus, (FIG. 10), in which the luciferase reporter expression is driven by the survivin promoter. See also, Zhu, et al., *Cancer Gene Therapy,* 11:256-262 (2004), and Houdt, et al., *J. Neurosurg.,* 104:583-592 (2006).

Other materials for preparing the disclosed constructs are also available and include, for example, BIRC5 (NM_001168) Human cDNA ORF Clone (Origene Catalogue Number RC205935), which is a BIRC5 (Myc-DDK-tagged)-Human baculoviral IAP repeat containing 5 (BIRC5/Survivin), transcript variant 1; pBS Survivin (Addgene Plasmid #19233), which is a pBluescript vector backbone including a *G. gallus* (chicken) survivin insert according to GenBank: FG356243.1 (PC/PO 2-94 Embryonic chicken perichondrium/periosteum library *Gallus gallus* cDNA clone PC/PO 2-94 5-similar to Baculoviral IAP repeat-containing 5 (survivin) (BIRC5), transcript variant 1, mRNA sequence) and Gene ID: 374078 (BIRC5 baculoviral IAP repeat containing 5 [*Gallus gallus* (chicken)]), each of which are specifically incorporated by reference in their entireties; and Luciferase-pcDNA3 (Addgene Plasmid #18964) which is a pcDNA3 including a Firefly Luciferase insert. Nucleic acid and protein sequences of all of the foregoing references, accession numbers, and reagents (e.g., plasmids and other vectors) are specifically incorporated by reference in their entireties.

B. Constructs for Treating Uterine Cancer

Constructs for treating uterine cancer include expression vectors under the control of a survivin promoter. The vectors can be prepared using materials and methods including those described above for the report constructs and others known in the art. However, it will be appreciated the therapeutic constructs optionally include a reporter gene (e.g., a reporter is not required for therapeutic constructs), and may further include additional elements not present in reporter constructs. The expression vectors can encode tumor suppressor genes, cytotoxic genes, cytostatic genes, cytokines, suicide genes, oncolytic virus and antigen-encoding genes. Examples of tumor suppressor genes include WT1, p53, p16, Rb, BRCA1, and LK8.

One embodiment provides a construct that expresses an oncolytic virus under the control of a survivin promoter. Oncolytic virus (OV) therapy is based on selective replication of viruses in cancer cells and their subsequent spread within a tumor without causing damage to normal tissue. Typically, OVs fall into two classes: (i) viruses that naturally replicate preferentially in cancer cells and are nonpathogenic in humans often due to elevated sensitivity to innate antiviral signaling or dependence on oncogenic signaling pathways. These include autonomous parvoviruses, myxoma virus (MYXV; poxvirus), Newcastle disease virus (NDV; paramyxovirus), reovirus, and Seneca valley virus (SVV; picornavirus); and (ii) viruses that are genetically manipulated for use as vaccine vectors, including measles virus (MV; paramyxovirus), poliovirus (PV; picornavirus), and vaccinia virus (VV; poxvirus), and/or those genetically engineered with mutations/deletions in genes required for replication in normal but not in cancer cells including adenovirus (Ad), herpes simplex virus (HSV), VV, and vesicular stomatitis virus (VSV; rhabdovirus).

C. Pharmaceutical Compositions

The nucleic acid constructs can be combined with a pharmaceutically acceptable excipient or carrier to form a pharmaceutically acceptable composition. Examples of suitable excipients or carriers include but are not limited to water, salt water, alcohol, lipid, wax, buffer solution, solid carrier such as mannitol, lactose, starches, magnesium stearate, sodium saccharin, talc, cellulose, glucose, sucrose, and magnesium carbonate, or biodegradable microsphere (e.g., polylactate polyglycolate).

The compositions may be provided in the form of single dose or multi-dose container such as sealed ampule or vial. Preferably, such container may be sealed so as to conserve aseptic condition of pharmaceutical formulations before using. In general, the formulation may be preserved as suspension, fluid, and emulsion in oil or aqueous vehicle. Further, the pharmaceutical formulation may be preserved under freeze drying conditions.

The pharmaceutical compositions may be administered with site-specific injection or intravenous injection. Site-specific injection includes, for example, intraperitoneal injection, intrapleural injection, intrathecal injection, intraarterial injection, intratumoral injection or local application. The preferred method is intravenous injection.

It should be understood that the suitable amount of the nucleic acid construct actually administered ought to be determined in light of various relevant factors including the condition to be treated, the age and weight of the individual patient, food, administration time, excretion rate, the severity of the patient's symptom and reaction susceptibility; and, therefore, the above dose should not be intended to limit the scope of the invention in any way. Generally, the adenoviral vector contained in the pharmaceutical composition may be administered in an appropriate physiologically acceptable carrier at a dose of about $10^4$ to about $10^{14}$ vp/mL. The multiplicity of infection may be generally in the range of 0.001 to 100, preferably 5, 10, 20, or 50. If administered as a polynucleotide construct, about 0.01 to 1000 μg/kg of an adenoviral vector can be administered. The adenoviral vector may be administered one or more time, depending upon the intended use and the immune response potential of the host, and may also be administered as multiple, simultaneous injections. If an immune response is undesirable, the immune response may be diminished by employing a variety of immunosuppressants, or by employing a technique such as an immunoadsorption procedure (e.g., immunoapheresis) that removes adenovirus antibody from the blood, so as to permit repetitive administration, without a strong immune response.

The composition may be used as the single therapy. But it may be combined with other anti-tumor protocols, such as conventional chemotherapy or radiation therapy for treating cancer. The chemotherapy drug which can be used with composition of the present invention encompasses paclitaxel, cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. The radiation therapy which can be used with the composition of the present invention may be X-ray irradiation and .gamma.-ray irradiation, etc.

The adenovirus produced from the adenoviral vector shows high oncolytic effect in tumor cells, while low effect in normal cells from in vitro and in vivo experiments. Thus, the viral vector comprising the tumor-specific promoter may be used for treating a cancer.

III. Methods for Detecting Uterine Cancer

One method for detecting uterine cancer includes contacting a cell or cells suspected of being cancerous with a vector containing a reporter gene, wherein the expression of the reporter gene is under the control of a survivin promoter. In a preferred embodiment, the vector is an adenoviral vector and the reporter gene encodes luciferase.

Another method provides administering to a subject suspected of having uterine cancer, an effective amount of a vector containing a reporter gene, wherein expression of the reporter gene is under the control of a survivin promoter. The vector can be administered systemically or directly into the uterus.

One embodiment provides a method for distinguishing cancerous uterine cells from non-cancerous uterine cells by contacting a population of uterine cells containing a mixture of cancerous and non-cancerous uterine cells with a vector containing a reporter gene, wherein the expression of the reporter gene is under the control of a survivin promoter, and detecting expression of the reporter gene wherein, expression of the reporter gene indicates that the cell expressing the reporter gene is cancerous. The contacting can be in vivo or ex vivo. Accordingly, methods of detecting uterine cancer in the subject and in tissue samples isolated from a subject are both specifically disclosed.

IV. Methods for Treating Uterine Cancer

One method for treating uterine cancer includes contacting a cell or cells suspected of being cancerous with a vector containing a gene that encodes tumor suppressor genes, cytotoxic genes, cytostatic genes, cytokines, suicide genes, oncolytic virus and antigen-encoding genes. Examples of tumor suppressor genes include WT1, p53, p16, Rb, BRCA1, and LK8. The expression of the gene is under the control of a survivin promoter. In a preferred embodiment, the vector is an adenoviral vector encoding an oncolytic virus, wherein the expression of the oncolytic virus is under the control of a survivin promoter.

Another method provides administering to a subject suspected of having uterine cancer, an effective amount of a vector encoding a cytotoxic agent, wherein expression of the cytotoxic agent is under the control of a survivin promoter. The vector can be administered systemically or directly into the uterus.

EXAMPLES

Example 1

X-Gal Staining

Materials and Methods

All procedures performed on animals were approved by Georgia Regents University's Institutional Animal Care and Use Committee and were within the guidelines of humane care of laboratory animals. Materials and methods used in viral vector construction, cell culture, and in vitro transfection experiments, s.c. Tumor and intrauterine models, and local vector administration, plasma collection, and statistical analyses are detailed herein materials and methods.

Recombinant Adenovirus and Promoters

Large-scale production of adenovirus vectors was performed as we have described previously with a typical batch yield of $2\times10^{10}$ plaque-forming units (PFU)/ml (Al-Hendy, A., et al., Am J Obstet Gynecol, 182(3): 553-559 (2000)). Ad vectors used in this study are listed in Table 1.

TABLE 1

Description of the Adenovirus vectors used in this study

| No. | virus | Promoter | Modification Site | Virus description |
|---|---|---|---|---|
| 1 | Ad5-luc | CMV | WILD | E1/E3 deleted, a luciferase gene under the CMV promoter in place of E1 |
| 2 | Ad5-LacZ | CMV | WILD | E1/E3 deleted, a luciferase gene under the CMV promoter in place of E1 |

TABLE 1-continued

Description of the Adenovirus vectors used in this study

| No. | virus | Promoter | Modification Site | Virus description |
| --- | --- | --- | --- | --- |
| 3 | Ad5-survivin-luc | Survivin | Promoter | E1/E3 deleted, a luciferase gene under the Survivin promoter in place of E1 |
| 4 | Ad5-heparanase-luc | Heparanase | Promoter | E1/E3 deleted, a luciferase gene under the heparanase promoter in place of E1 |
| 5 | Ad5-SLPI-uc | Secretory leukoprotease Inhibitor (SLPI) | Promoter | E1/E3 deleted, a luciferase gene under the SLPI promoter in place of E1 |

No. 1 is described in Krasnykh, V. N., et al., J Virol 70(10): 6839-6846 (1996).
No. 2 is described in Franklin, R., M. Quick and G. Haase, Gene Ther 6(8): 1360-1367 (1999).
No. 3 is described in Van Houdt, W. J., et al., J Neurosurg 104(4): 583-592 (2006).
No. 4 is described in Breidenbach, M., et al., Cancer Lett 240(1): 114-122 (2006).
No. 5 is described in Barker, S. D., et al., Gene Ther 10(14): 1198-1204 (2003). *Cell cultures*

For experimental models, the human leiomyosarcoma cell line SKUT-1 was used and purchased from American type Culture collection (ATCC® HTB-114™) that is derived from 75 years old Caucasian female originating from grade III, mesodermal tumor (mixed); consistent with uterine leiomyosarcoma.

The cells are considered biosafety level 1 based on U.S. Public Health Service Guidelines. Primary cultures of human leiomyoma cells were derived from fibroid tumors removed during hysterectomies. Human leiomyoma tissues were collected according to the policies of the Institutional Review Board of Georgia Regents University, Augusta, Ga., USA, and used to establish primary fibroid (1ry F) cells, as described previously (Rauk, P. N., et al, Am J Obstet Gynecol 173(2): 571-577 (1995); Al-Hendy, A., et al., Am J Obstet Gynecol 191(5): 1621-1631 (2004)). To represent normal cells (controls), we used a human myometrial cell line (Myo N); this cell line was cultured and maintained as described previously (Carney, M. E. Hawaii Med J 61(12): 283-286 (2002)).

X Gal Staining of Fixed Leiomyosarcoma Cells

This experiment was done to evaluate the susceptibility of SKUT-1 cells to transfection by wild type Adenovirus serotype 5 with B-Galactosidase as a reporter gene. Three different multiplicities of infection (MOI) of 1, 3, and 5 were used. The viral particles were mixed with cell culture media followed by 1 hour of mild shaking then regular cell culture conditions were applied. 24 hours later, X-Gal staining was performed on the cells.

Results

Human Leiomyosarcoma cells (LMS) are susceptible to wild type adenovirus transfection by X-Gal Staining. The transgene of the bacterial enzyme β-galactosidase can be easily located with a LacZ stain using the artificial substrate X-Gal, which turns blue when it is cleaved by B-Galactosidase. Culture media was aspirated off and washed SKUT-1 cells 1× with cold PBS, fixed the cells on ice with ~5 mL glutaraldehyde (1:100 dilution of stock in PBS) for 5 min, rinse the cells 3× with PBS for 4 min. per wash, dilute 25× stock of X-Gal into the staining solution (final 1 mg/mL of X-gal), add ~5 mL of the X-gal staining solution to the cells and incubate at 37° C. for 24 hours. Cells were checked every 4 hours to determine whether cells were turning blue. (FIGS. 1A-1C) Transfection of Leiomyosarcoma cells by Ad-lacZ, X-Gal staining of human SK-UT 1 cells after transfection with Adenovirus with Ad-Lac Z reporter gene at multiplicity of infection 1 MOI (FIG. 1A), 3 MOI (FIG. 1B) and 5 MOI (FIG. 1C). X-gal is an analogue of lactose and therefore hydrolyzed by the β-galactosidase enzyme giving intensely blue products.

Example 2

Screening for Sarcoma Specific Gene Expression

Materials and Methods

Luciferase Assay

To screen the 3 promoters of interest for their sarcoma specific gene expression potential, #3 60 mm$^2$ cell culture dishes of SKUT-1 cells at 70% confluence were transfected with 3 different adenoviral constructs which are Ad Survivin, Ad Heparanase, and Ad SLPI all at the same MOI the same technique as described above and used luciferase assay to differentiate between gene expression levels under the control of the 3 used promoters. Growth medium was removed from cultured cells, and the cells were rinsed in 1× PBS. Then without dislodging cells, as much of the final wash was removed as possible. 400 ul volume of 1× cell lysis buffer was dispensed (CCLR) into each culture vessel then attached cells were scraped from the dish, and the cells and solution were transferred to a microcentrifuge tube. Debris was separated by brief centrifugation, and the supernatant was transferred to a new tube. 20 µl of cell lysate was used with 100 µl of luciferase assay reagent and measured the light produced by Synergy HT microplate reader utilizing Gen-5 software for bioluminescence detection. The classic luciferase assay was used to compare the degree of reporter gene expression in leiomyosarcoma cells under different promoters.

Results

Figure 2:
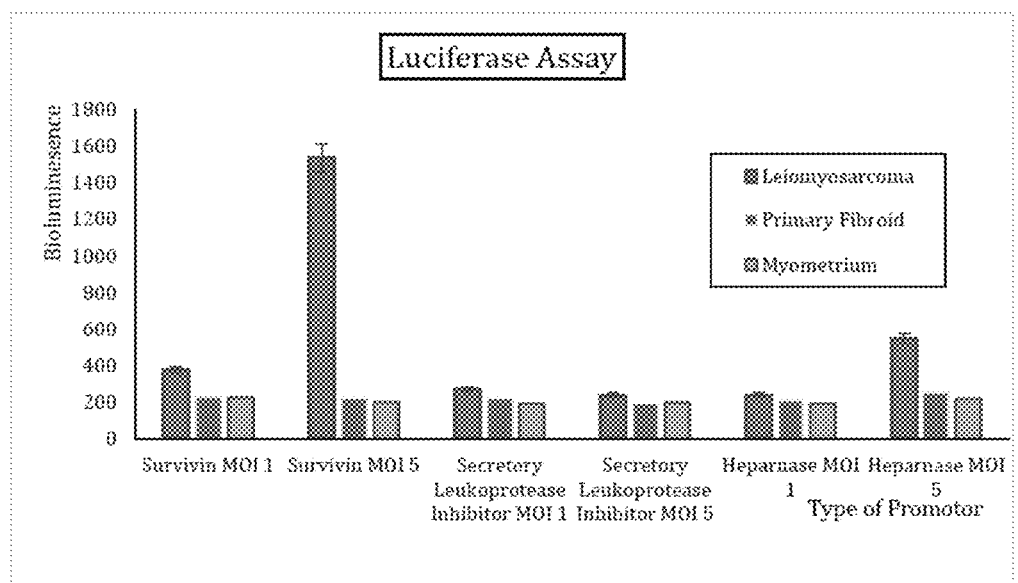
FIG. 2 shows the results of the luciferase assay in Leiomyosarcoma tissue, primary fibroid tissue, and myometrium transfected with constructs having a Survivin promoter at 1 MOI, Survivin promoter at 5 MOI, Secretory Leukoprotease Inhibitor promoter at 1 MOI, Secretory Leukoprotease Inhibitor promoter at 5 MOI, Heparanase promoter at 1 MOI, Heparanase promoter at 5 MOI.

Screening of reporter gene expression in LMS cells under different promoters reveals Ad-Survivin as a malignancy specific promoter "Luciferase assay." FIG. 2 shows the results of the luciferase assay in Leiomyosarcoma tissue, primary fibroid tissue, and myometrium transfected with constructs having a Survivin promoter at 1 MOI, Survivin promoter at 5 MOI, Secretory Leukoprotease Inhibitor promoter at 1 MOI, Secretory Leukoprotease Inhibitor promoter at 5 MOI, Heparanase promoter at 1 MOI, Heparanase promoter at 5 MOI.

Example 3

In Vitro Bioluminescence Imaging

Materials and Methods
Animal Model

SKUT-1, 1ry F, Myo N cells (5×10⁶ or 20×10⁶) were either implanted directly or transfected with Adenovirus first then implanted into the right flank of female nude mice (Nu/Nu; Harlan Laboratory), and tumors developed over a period of 3-5 days.

Luciferin D In Vitro Bioluminescence Imaging

To confirm the superior Ad Survivin controlled reporter gene expression by IVIS live cell-imaging, the same number of cells were transfected and imaged using Xenogen IVIS 100 (Caliper Life Sciences, Hopkinton, Mass.), an optical imaging device with extremely light-tight, low background imaging chamber. The device was used for in vitro, ex vivo, and in vivo bioluminescence detection. Firefly D-Luciferin 15 mg/ml in PBS was added to cell culture media in culture dishes. The software mode was set to luminescence, photography and X-ray. Exposure was 600 with low binning (Henriques, Henriques-Pons, et al. 2014). SKUT-1 Cells are highly expressing luciferase enzyme under survivin promoter in comparison to benign tumor cells as well as healthy myometrial cells in vitro by "IVIS Live cell Bioimaging"

Results

Figure 3:
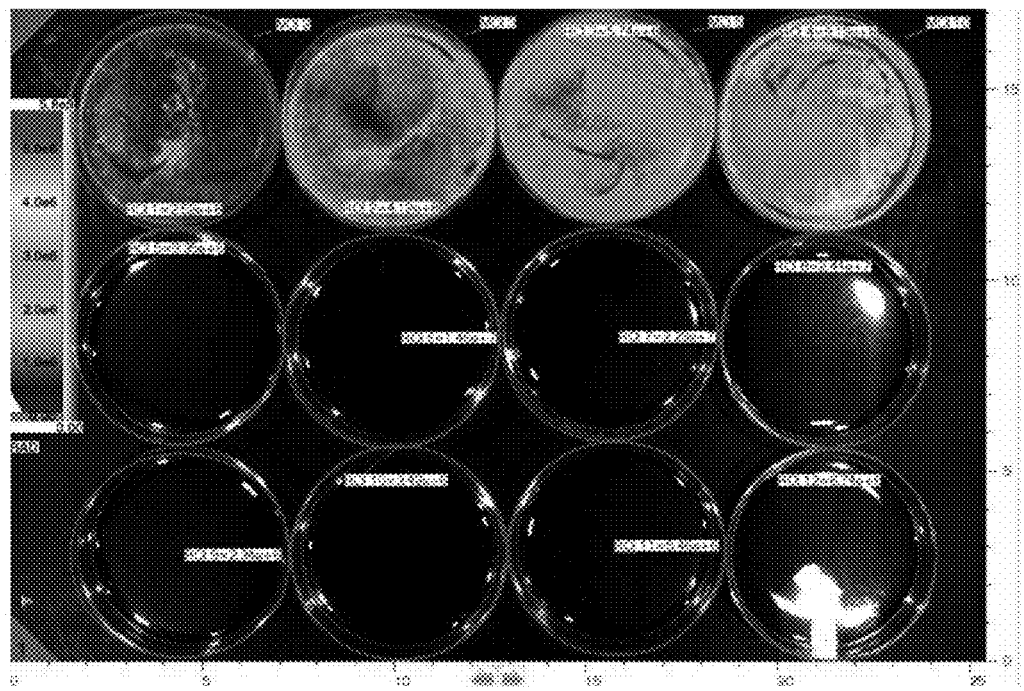
FIG. 3 is an image of three rows of cell culture plates. The first row from top to bottom is Leiomyosarcoma, the second row is primary fibroid, and the third row is myometrium all transfected with a vector having the survivin promoter controlling expression of luciferase. MOI for each column of plates from left to right is 2, 3, 5, and 10.
Figure 4:
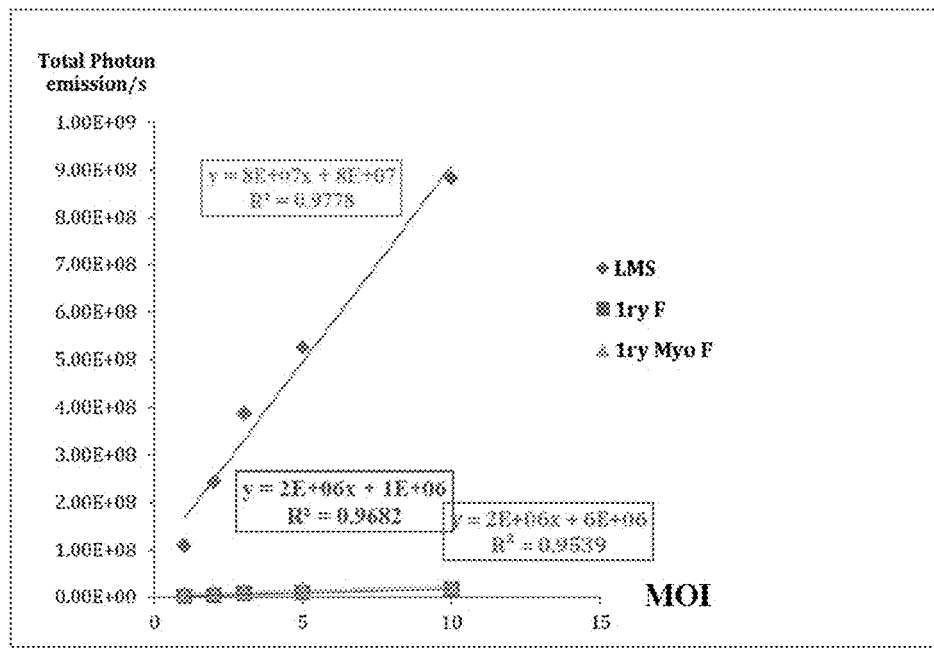
FIG. 4 is a line graph of total photon emission/s versus MOI for LMS (♦), 1ryF (■) or 1ryMyoF (triangle) cell lines infected with Ad5-Survivin-luc.

SKUT-1 Cells highly express luciferase enzyme under survivin promoter control in comparison to benign tumor cells as well as healthy myometrial cells in vitro by "IVIS Live cell Bioimaging" (FIG. 3). The order of dishes is Leiomyosarcoma, Primary Fibroid and Myometrium respectively. FIG. 4 shows the correlation of the total photon emission/second to the MOI of the different studied cell lines.

Example 4

Ex Vivo and In Vivo Bioluminescence Imaging

Materials and Methods
Luciferin-D Ex Vivo and In Vivo Bioluminescence Imaging

Either ex vivo or in vivo transfection was utilized in animal studies. In the ex vivo case, transfected cells were implanted in the animals either subcutaneously or intrauterine. Untransfected cells were implanted in the nude mice and then, when the tumor developed the virus was injected intravenously. D-Luciferin 15 mg/ml in PBS was intraperitoneally injected at 260 ul per mouse followed by isofluran inhalation anesthesia 10 minutes later. The anesthetized animals were then placed in the IVIS chamber. The software mode was set to luminescence, photography and X-ray. Exposure was 600 with low binning. (Henriques, C., et al., Parasit Vectors 7: 89 (2014)).

Results

Figures 5A, 5B:
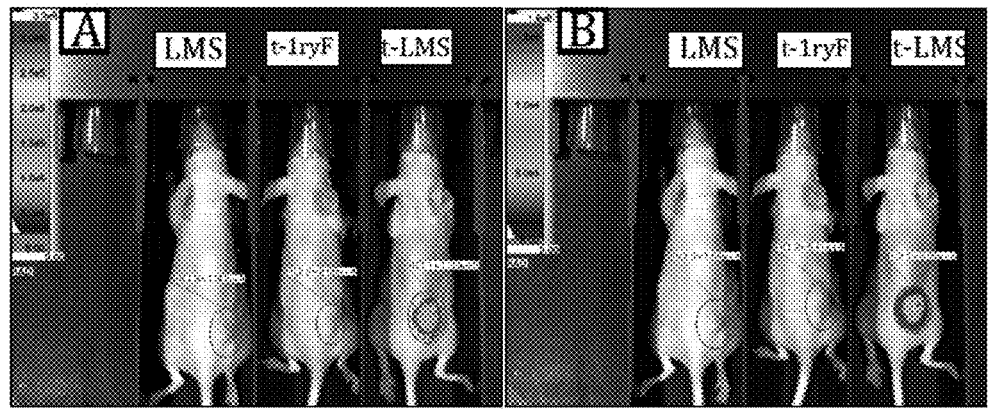
FIGS. 5A and 5B are photographs of mice injected with $5 \times 10^6$ cells transfected with Ad5-Survivin-luc. Signal shows only in the transfected LMS lesions and near zero in the non-transfected as well as the begin leiomyoma case. (P<0.0001)

Ex vivo bioimaging of subcutaneously injected cells shows higher expression in LMS compared to benign and normal cells (FIGS. 5A and 5B). Ex-vivo subcutaneous model Bioluminescence imaging at 5×10⁶ cells per animal thirty minutes (FIG. 5A) and one hour (FIG. 5B) post D-luciferin injection. Showing signal only in the transfected LMS lesions and is near zero in the non-transfected as well as the begin leiomyoma case. (P<0.0001)

Figures 6A, 6B, 6C:
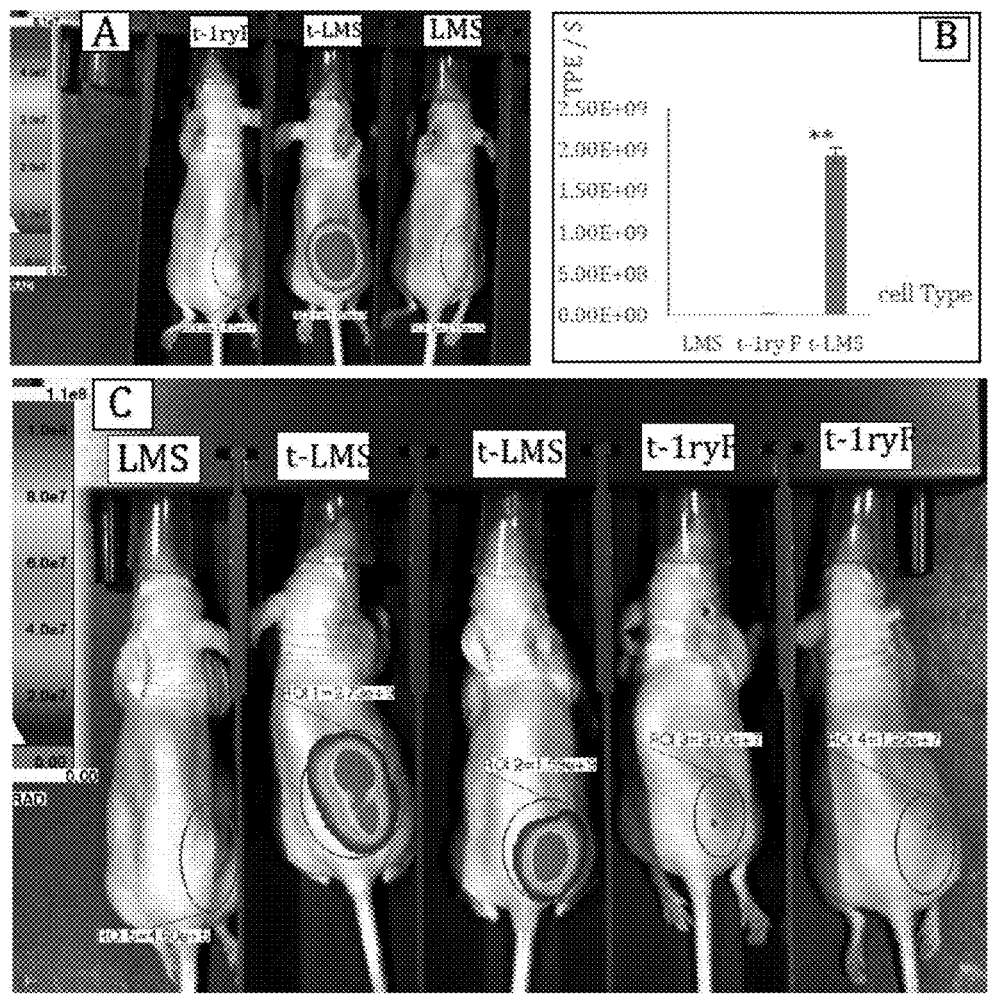
FIG. 6A is a photograph of mice injected with $20 \times 10^6$ transfected t-1ryF cells, transfected t-LMS cells, or LMS cells. Signal shows only on transfected t-LMS cells.
FIG. 6B is bar graph of total photon emission (TPE) per second of LMS cells, t-1ryF cells, and t-LMS cells.
FIG. 6C is a photograph of mice injected with LMS cells, t-LMS cells, t-LMS cells, t-1ryF cells, or t-1ryF cells

In vivo Bioimaging showing Leiomyosarcoma lesions emits significantly higher luminescence compared to benign and normal tissue (FIGS. 6A-6C). Bioluminescence imaging subcutaneously injected with 20×10⁶ cells per animal transfected with Ad5-Survivin-luc. Signal shows only in the transfected LMS lesions and is near zero in the non-transfected as well as the begin leiomyoma case. (P<0.0001).

Figures 7A, 7B, 7C, 7D:
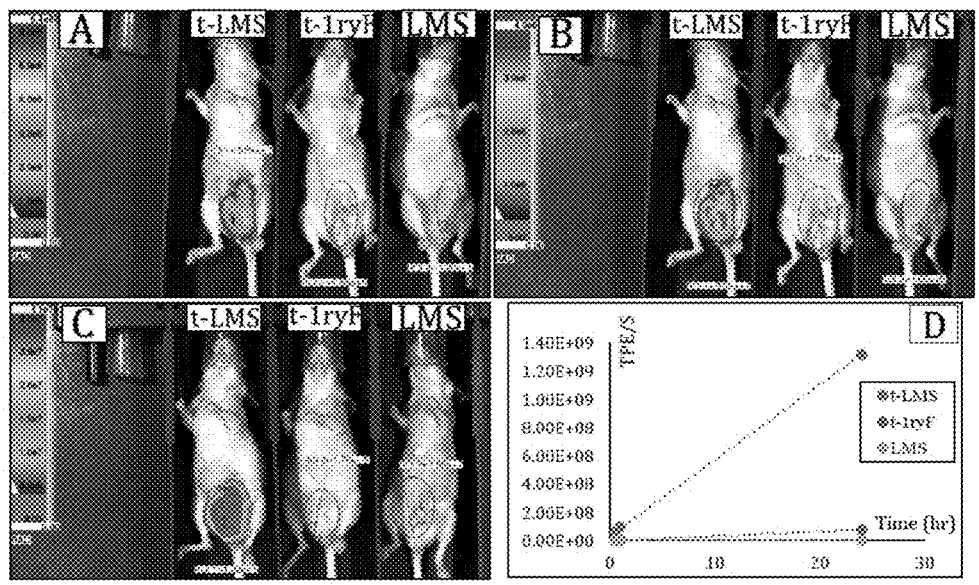
FIGS. 7A-7B show images of mice with $20 \times 10^6$ cells injected intracervically. The cells are t-LMS, t-1ryF, or LMS cells.
FIG. 7C shows images post cellular implantation with the same number of cells.
FIG. 7D is line graph of total photon emission per second versus time for from top to bottom t-LMS, t-1ryF, and LMS cells.

FIGS. 7A-7B show images of mice with 20×10⁶ cells injected intracervically. The cells are t-LMS, t-1ryF, or LMS cells. FIG. 7A is shows images thirty minutes post injection. FIG. 7B shows images one hour post injection, and FIG. 7C shows images post cellular implantation with the same number of cells. FIG. 7D is line graph of total photon emission per second versus time for from top to bottom t-LMS, t-1ryF, and LMS cells.

Figure 8:
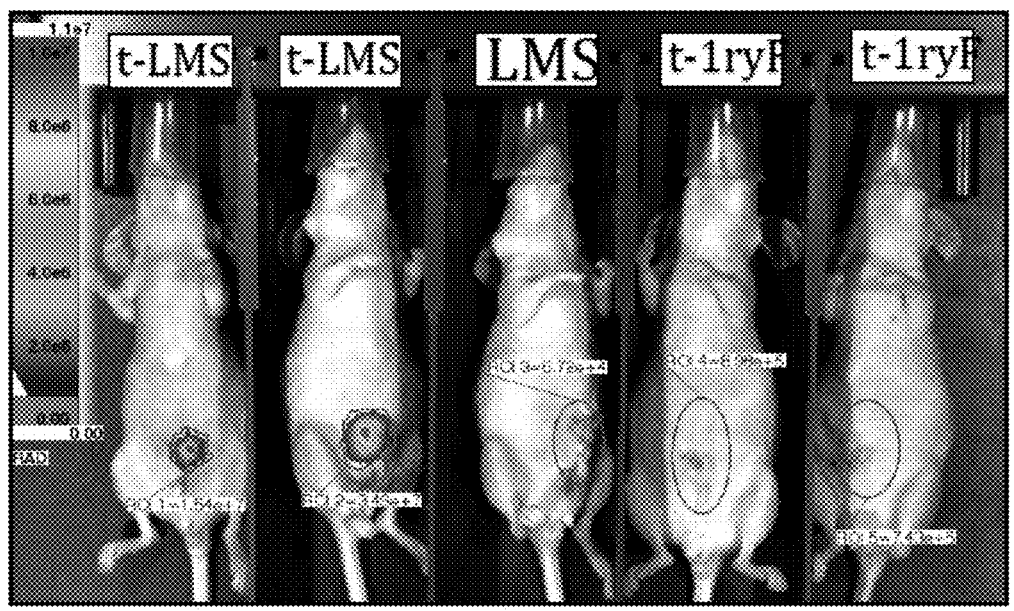
FIG. 8 is an image of mice injected with $5 \times 10^6$ cells intracervically. The cells are t-LMS, t-LMS, LMS, t-1ryF, and t-1ryF cells from left to right. Signal shows only in the infected LMS lesions and is near zero in the non-transfected as well as benign leiomyoma case.

FIG. 8 is an image of mice injected with 5×10⁶ cells intracervically. The cells are t-LMS, t-LMS, LMS, t-1ryF, and t-1ryF cells from left to right. Signal shows only in the infected LMS lesions and is near zero in the non-transfected as well as benign leiomyoma case.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of detecting uterine cancer cells comprising:
   transfecting uterine cells suspected of being cancerous with a vector comprising a survivin promoter controlling the expression of a reporter gene; and
   detecting the expression of the reporting gene, wherein expression of the reporter gene indicates the presence of uterine cancer cells,
   wherein the vector comprises a survivin promoter nucleic acid sequence according to SEQ ID NO:1.

2. The method of claim 1, wherein the uterine cancer cells are leiomyosarcoma cells.

3. The method of claim 1, wherein the reporter gene encodes luciferase.

4. The method of claim 1, wherein the vector is a viral vector.

5. The method of claim 4, wherein the vector is selected from the group consisting of adenovirus, adeno-associated virus, retrovirus, lentivirus, herpes simplex virus, and reovirus.

* * * * *

SEQUENCE LISTING

```
<160> NUMBER OF SEQ ID NOS: 6

<210> SEQ ID NO 1
<211> LENGTH: 1595
<212> TYPE: DNA
<213> ORGANISM: Homo sapiens

<400> SEQUENCE: 1
aaattgacat cgggccgggc gcagtggctc acatctgtaa tcccagcact tgggaggcc      60 gaggcaggca gatcacttga ggtcaggagt ttgagaccag cctggcaaac atggtgaaac     120
cccatctcta ctaaaaatac aaaaattagc ctggtgtggt ggtgcatgcc tttaatctca     180
gctactcggg aggctgaggc aggagaatcg cttgaacccg tggcggggag gaggttgcag     240
```

```
tgagctgaga tcatgccact gcactccagc ctgggcgata gagcgagact cagtttcaaa    300
taaataaata aacatcaaaa taaaaagtta ctgtattaaa gaatgggggc ggggtgggag    360
gggtggggag aggttgcaaa aataaataaa taaataaata aaccccaaaa tgaaaaagac    420
agtggaggca ccaggcctgc gtggggctgg agggctaata aggccaggcc tcttatctct    480
ggccatagaa ccagagaagt gagtggatgt gatgcccagc tccagaagtg actccagaac    540
accctgttcc aaagcagagg acacactgat ttttttttta ataggctgca ggacttactg    600
ttggtgggac gccctgcttt gcgaagggaa aggaggagtt tgccctgagc acaggccccc    660
accctccact gggctttccc cagctccctt gtcttcttat cacggtagtg gcccagtccc    720
tggcccctga ctccagaagg tggccctcct ggaaacccag gtcgtgcagt caacgatgta    780
ctcgccggga cagcgatgtc tgctgcactc catccctccc ctgttcattt gtccttcatg    840
cccgtctgga gtagatgctt tttgcagagg tggcaccctg taaagctctc ctgtctgact    900
tttttttttt ttttagactg agttttgctc ttgttgccta ggctggagtg caatggcaca    960
atctcagctc actgcaccct gcctcccg ggttcaagcg attctcctgc ctcagcctcc    1020
cgagtagttg ggattacagg catgcaccac cacgcccagc taattttttgt attttttagta    1080 gagacaaggt ttcaccgtga tggccaggct ggtcttgaac tccaggactc aagtgatgct    1140
cctgcctagg cctctcaaag tgttgggatt acaggcgtga gccactgcac ccggcctgca    1200
cgcgttgttt gaaagcagtc gagggggcgc taggtgtggg cagggacgag ctggcgcggc    1260
gtcgctgggt gcaccgcgac cacgggcaga gccacgcggc gggaggacta caactcccgg    1320 cacacccgc gccgccccgc tctactccc agaaggccgc gggggtgga ccgcctaaga    1380 gggcgtgcgc tcccgacatg ccccgcggcg cgccattaac cgccagattt gaatcgcggg    1440
acccgttggc agaggtggcg gcggcggcat gggtgccccg acgttgcccc ctgcctggca    1500
gccctttctc aaggaccacc gcatctctac attcaagaac tggcccttct tggagggctg    1560
cgcctgcacc ccggagcggg tgagactgcc cggcc                              1595
```

<210> SEQ ID NO 2
<211> LENGTH: 550
<212> TYPE: PRT
<213> ORGANISM: Artificial Sequence
<220> FEATURE:
<223> OTHER INFORMATION: Luciferase Polypeptide sequence

<400> SEQUENCE: 2

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
```

```
            115                 120                 125
Ser Lys Lys Gly Leu Gln Lys Ile Leu Asn Val Gln Lys Lys Leu Pro
            130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
                195                 200                 205
Ala Leu Pro His Arg Thr Ala Cys Val Arg Phe Ser His Ala Arg Asp
            210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
            275                 280                 285
Pro Thr Leu Phe Ser Phe Phe Ala Lys Ser Thr Leu Ile Asp Lys Tyr
            290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
            370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
            450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
                500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
            530                 535                 540
```

Gly Gly Lys Ile Ala Val
545             550

<210> SEQ ID NO 3
<211> LENGTH: 37
<212> TYPE: PRT
<213> ORGANISM: Homo sapiens

<400> SEQUENCE: 3

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg
        35

<210> SEQ ID NO 4
<211> LENGTH: 14796
<212> TYPE: DNA
<213> ORGANISM: Homo sapiens

<400> SEQUENCE: 4

| | |
|---|---|
| tctagacatg cggatatatt caagctgggc acagcacagc agccccaccc caggcagctt | 60 |
| gaaatcagag ctggggtcca aagggaccac accccgaggg actgtgtggg ggtcggggca | 120 |
| cacaggccac tgcttccccc cgtctttctc agccattcct gaagtcagcc tcactctgct | 180 |
| tctcagggat ttcaaatgtg cagagactct ggcacttttg tagaagcccc ttctggtcct | 240 |
| aacttacacc tggatgctgt ggggctgcag ctgctgctcg ggctcgggag gatgctgggg | 300 |
| gcccggtgcc catgagcttt tgaagctcct ggaactcggt tttgagggtg ttcaggtcca | 360 |
| ggtggacacc tgggctgtcc ttgtccatgc atttgatgac attgtgtgca gaagtgaaaa | 420 |
| ggagttaggc cgggcatgct ggcttatgcc tgtaatccca gcactttggg aggctgaggc | 480 |
| gggtggatca cgaggtcagg agttcaatac cagcctggcc aagatggtga accccgtctc | 540 |
| tactaaaaaa tacaaaaaaa ttagccgggc atggtggcgg cgcatgtaa tcccagctac | 600 |
| tgggggggct gaggcagaga attgctgaa cccaggagat ggaggttgca gtgagccaag | 660 |
| attgtgccac tgcactgcac tccagcctgg cgacagagca agactctgtc tcaaaaaaaa | 720 |
| aaaaaaaaag tgaaaggag ttgttccttt cctccctcct gagggcaggc aactgctgcg | 780 |
| gttgccagtg gaggtggtgc gtccttggtc tgtgcctggg ggccacccca gcagaggcca | 840 |
| tggtggtgcc agggcccggt tagcgagcca atcagcagga cccaggggcg acctgccaaa | 900 |
| gtcaactgga tttgataact gcagcgaagt taagtttcct gattttgatg attgtgttgt | 960 |
| ggttgtgtaa gagaatgaag tatttcgggg tagtatggta atgccttcaa cttacaaacg | 1020 |
| gttcaggtaa accacccata tacatacata tacatgcatg tgatatatac acatacaggg | 1080 |
| atgtgtgtgt gttcacatat atgaggggag agagactagg ggagagaaag taggttgggg | 1140 |
| agagggagag agaaaggaaa acaggagaca gagagagagc ggggagtaga gagagggaag | 1200 |
| gggtaagaga gggagaggag gagagaaagg gaggaagaag cagagagtga atgttaaagg | 1260 |
| aaacaggcaa aacataaaca gaaaatctgg gtgaagggta tatgagtatt ctttgtacta | 1320 |
| ttcttgcaat tatctttat ttaaattgac atcgggccgg gcgcagtggc tcacatctgt | 1380 |
| aatcccagca ctttgggagg ccgaggcagg cagatcactt gaggtcagga gtttgagacc | 1440 |
| agcctggcaa acatggtgaa accccatctc tactaaaaat acaaaaatta gcctggtgtg | 1500 |

```
gtggtgcatg cctttaatct cagctactcg ggaggctgag gcaggagaat cgcttgaacc    1560
cgtggcgggg aggaggttgc agtgagctga gatcatgcca ctgcactcca gcctgggcga    1620
tagagcgaga ctcagtttca aataaataaa taaacatcaa aataaaaagt tactgtatta    1680
aagaatgggg gcggggtggg aggggtgggg agaggttgca aaaataaata aataaataaa    1740
taaaccccaa aatgaaaaag acagtggagg caccaggcct gcgtgggggct ggagggctaa   1800 taaggccagg cctcttatct ctggccatag aaccagagaa gtgagtggat gtgatgccca    1860
gctccagaag tgactccaga cacctgtt ccaaagcaga ggacacactg atttttttt       1920 taataggctg caggacttac tgttggtggg acgccctgct ttgcgaaggg aaaggaggag    1980
tttgccctga gcacaggccc ccacccttcca ctgggctttc cccagctccc ttgtcttctt   2040
atcacggtag tggcccagtc cctgcccct gactccagaa ggtggccctc ctggaaaccc     2100
aggtcgtgca gtcaacgatg tactcgccgg acagcgatg tctgctgcac tccatccctc    2160
ccctgttcat ttgtccttca tgcccgtctg gagtagatgc ttttttgcaga ggtggcaccc  2220 tgtaaagctc tcctgtctga cttttttttt tttttagac tgagttttgc tcttgttgcc    2280
taggctggag tgcaatggca caatctcagc tcactgcacc ctctgcctcc cgggttcaag   2340
cgattctcct gcctcagcct cccgagtagt tgggattaca ggcatgcacc accacgccca   2400
gctaattttt gtattttag tagagacaag gtttcaccgt gatggccagg ctggtcttga    2460
actccaggac tcaagtgatg ctcctgccta ggcctctcaa agtgttggga ttacaggcgt   2520
gagccactgc acccggcctg cacgcgttct ttgaaagcag tcgagggggc gctaggtgtg   2580
ggcagggacg agctggcgcg gcgtcgctgg gtgcaccgcg accacgggca gagccacgcg   2640
gcgggaggac tacaactccc ggcacacccc gcgccgcccc gcctctactc ccagaaggcc   2700 gcgggggggtg gaccgcctaa gagggcgtgc gctcccgaca tgccccgcgg cgcgccatta  2760
accgccagat ttgaatcgcg ggacccgttg gcagaggtgg cggcggcggc atgggtgccc   2820
cgacgttgcc ccctgcctgg cagccctttc tcaaggacca ccgcatctct acattcaaga   2880
actggccctt cttggagggc tgcgcctgca ccccggagcg ggtgagactg cccggcctcc   2940
tggggtcccc cacgcccgcc ttgccctgtc cctagcgagg ccactgtgac tgggcctcgg   3000
gggtacaagc cgccctcccc tccccgtcct gtccccagcg aggccactgt ggctgggccc   3060
cttgggtcca ggccggcctc ccctccctgc tttgtcccca tcgaggcctt tgtggctggg   3120
cctcggggtt ccgggctgcc acgtccactc acgagctgtg ctgtcccttg cagatggccg   3180
aggctggctt catccactgc cccactgaga acgagccaga cttggcccag tgtttcttct   3240
gcttcaagga gctggaaggc tgggagccag atgacgaccc catgtaagtc ttctctggcc   3300
agcctcgatg ggctttgttt tgaactgagt tgtcaaaaga tttgagttgc aaagacactt   3360
agtatgggag ggttgctttc caccctcatt gcttcttaaa cagctgttgt gaacggatac   3420
ctctctatat gctggtgcct tggtgatgct tacaacctaa ttaaatctca tttgaccaaa   3480
atgccttggg gtggacgtaa gatgcctgat gcctttcatg ttcaacagaa tacatcagca   3540
gaccctgttg ttgtgaactc ccaggaatgt ccaagtgctt tttttgagat tttttaaaaa   3600
acagtttaat tgaaatataa cctacacagc acaaaaatta ccctttgaaa gtgtgcactt   3660
cacactttcg gaggctgagg cgggcggatc acctgaggtc aggagttcaa gacctgcctg   3720
gccaacttgg cgaaacccccg tctctactaa aaatacaaaa attagccggg catggtagcg   3780
cacgcccgta atcccagcta ctcgggaggc taaggcagga gaatcgcttg aacctgggag   3840
gcggaggttg cagtgagccg agattgtgcc aatgcactcc agcctcggcg acagagcgag   3900
```

```
actccgtcat aaaaataaaa aattgaaaaa aaaaaaagaa agaaagcata tacttcagtg    3960
ttgttctgga ttttttttctt caagatgcct agttaatgac aatgaaattc tgtactcgga   4020
tggtatctgt ctttccacac tgtaatgcca tattctttc tcacctttt ttctgtcgga     4080
ttcagttgct tccacagctt taatttttt cccctggaga atcaccccag ttgttttct     4140
ttttggccag aagagagtag ctgtttttt tcttagtatg tttgctatgg tggttatact    4200
gcatccccgt aatcactggg aaagatcag tggtattctt cttgaaaatg aataagtgtt    4260
atgatatttt cagattagag ttacaactgg ctgtcttttt ggactttgtg tggccatgtt   4320
ttcattgtaa tgcagttctg gtaacggtga tagtcagtta tacagggaga ctcccctagc   4380
agaaaatgag agtgtgagct agggggtccc ttggggaacc cggggcaata atgcccttct   4440
ctgcccttaa tccttacagt gggccgggca cggtggctta cgcctgtaat accagcactt   4500
tgggaggccg aggcgggcgg atcacgaggt caggagatcg agaccatctt ggctaatacg   4560
gtgaaacccc gtctccacta aaaatacaaa aaattagccg ggcgtggtgg tgggcgcctg   4620
tagtcccagc tactcgggag gctgaggcag gagaatggcg tgaacccagg aggcggagct   4680
tgcagtgagc cgagattgca ccactgcact ccagcctggg cgacagaatg agactccgtc   4740
tcaaaaaaaa aaaaaaaga aaaaaatctt tacagtggat tacataacaa ttccagtgaa    4800
atgaaattac ttcaaacagt tccttgagaa tgttggaggg atttgacatg taattccttt    4860
ggacatatac catgtaacac ttttccaact aattgctaag gaagtccaga taaaatagat    4920
acattagcca cacagatgtg gggggagatg tccacaggga gagagaaggt gctaagaggt    4980
gccatatggg aatgtggctt gggcaaagca ctgatgccat caacttcaga cttgacgtct    5040
tactcctgag gcagagcagg gtgtgcctgt ggagggcgtg gggaggtggc ccgtggggag    5100
tggactgccg ctttaatccc ttcagctgcc tttccgctgt tgttttgatt tttctagaga    5160
ggaacataaa aagcattcgt ccggttcgc tttcctttct gtcaagaagc agtttgaaga    5220
attaacccctt ggtgaatttt tgaaactgga cagagaaaga gccaagaaca aaattgtatg   5280
tattgggaat aagaactgct caaaccctgt tcaatgtctt tagcactaaa ctacctagtc    5340
cctcaaaggg actctgtgtt ttcctcagga agcattttt tttttttct gagatagagt     5400
ttcactcttg ttgcccaggc tggagtgcaa tggtgcaatc ttggctcact gcaacctctg    5460
cctctcgggt tcaagtgatt ctcctgcctc agcctcccaa gtaactggga ttacaggaa    5520
gtgccaccac acccagctaa ttttttgtatt tttagtagag atggggtttc accacattgc   5580
ccaggctggt cttgaactcc tgacctcgtg attcgcccac cttggcctcc caagtgctg    5640
ggattacagg cgtgaaccac cacgcctggc ttttttttt ttgttctgag acacagtttc    5700
actctgttac ccaggctgga gtaggtggc ctgatctcgg atcactgcaa cctccgcctc    5760
ctgggctcaa gtgatttgcc tgcttcagcc tcccaagtag ccgagattac aggcatgtgc    5820
caccacaccc aggtaatttt tgtattttg gtagagacga ggtttcacca tgttggccag    5880
gctggttttg aactcctgac ctcaggtgat ccacccgcct cagcctccca aagtgctgag   5940
attataggtg tgagccacca cacctggcct caggaagtat tttattttt aaatttattt    6000
atttatttga gatggagtct tgctctgtcg cccaggctag agtgcagcga cgggatctcg    6060
gctcactgca agctccgccc ccaggttca agccattctc ctgcctcagc ctcccgagta    6120
gctgggacta caggcgcccg ccaccacacc cggctaattt ttttgtattt ttagtagaga    6180
cgggttttca ccgtgttagc caggagggtc ttgatctcct gacctcgtga tctgcctgcc    6240
```

```
tcggcctccc aaagtgctgg gattacaggt gtgagccacc acacccggct attttttattt    6300 ttttgagaca gggactcact ctgtcacctg gctgcagtg cagtggtaca ccatagctca      6360
ctgcagcctc gaactcctga gctcaagtga tcctcccacc tcatcctcac aagtaattgg     6420
gactacaggt gcaccccacc atgcccacct aatttattta tttatttatt tatttatttt     6480
catagagatg agggttccct gtgttgtcca ggctggtctt gaactcctga gctcacggga     6540
tccttttgcc tgggcctccc aaagtgctga gattacaggc atgagccacc gtgcccagct     6600
aggaatcatt tttaaagccc ctaggatgtc tgtgtgattt aaagctcct ggagtgtggc      6660 cggtataagt atataccggt ataagtaaat cccacatttt gtgtcagtat ttactagaaa     6720
cttagtcatt tatctgaagt tgaaatgtaa ctgggcttta tttatttatt tatttattta    6780
tttattttta attttttttt ttgagacgag tctcactttg tcacccaggc tggagtgcag     6840
tggcacgatc tcggctcact gcaacctctg cctcccgggg tcaagcgatt ctcctgcctt     6900
agcctcccga gtagctggga ctacaggcac gcaccaccat gcctggctaa tttttgtatt     6960
tttagtagac ggggtttcac catgctggcc aagctggtct caaactcctg accttgtgat     7020
ctgcccgctt tagcctccca gagtgctggg attacaggca tgagccacca tgcgtggtct     7080
ttttaaaatt ttttgatttt ttttttttt gagacagagc cttgctctgt cgcccaggct      7140
ggagtgcagt ggcacgatct cagctcacta caagctccgc ctcccgggtt cacgccattc     7200
ttctgcctca gcctcctgag tagctgggac tacaggtgcc caccaccacg cctggctaat     7260 ttttttggt attttatta gagacaaggt ttcatcatgt tggccaggct ggtctcaaac       7320
tcctgacctc aagtgatctg cctgcctcgg cctcccaaag cgctgagatt acaggtgtga     7380
tctactgcgc caggcctggg cgtcatatat tcttatttgc taagtctggc agccccacac     7440
agaataagta ctgggggatt ccatatcctt gtagcaaagc cctgggtgga gagtcaggag     7500
atgttgtagt tctgtctctg ccacttgcag actttgagtt taagccagtc gtgctcatgc     7560
tttccttgct aaatagaggt tagacccct atcccatggt ttctcaggtt gcttttcagc      7620
ttgaaaattg tattcctttg tagagatcag cgtaaaataa ttctgtcctt atatgtggct     7680
ttattttaat ttgagacaga gtgtcactca gtcgcccagg ctggagtgtg gtggtgcgat     7740
cttggctcac tgcgacctcc acctcccagg ttcaagcgat tctcgtgcct caggctccca    7800
agtagctgag attataggtg tgtgccacca ggcccagcta acttttgtat ttttagtaga    7860
gacagggttt tgccatgttg ctaagctgg tctcgaactc ctggcctcaa gtgatctgcc     7920
cgccttggca tcccaaagtg ctgggattac aggtgtgaac caccacct ggcctcaata      7980 tagtggcttt taagtgctaa ggactgagat tgtgttttgt caggaagagg ccagttgtgg    8040
gtgaagcatg ctgtgagaga gcttgtcacc tggttgaggt tgtgggagct gcagcgtggg    8100
aactggaaag tgggctgggg atcatctttt tccaggtcag gggtcagcca gcttttctgc    8160
agcgtgccat agaccatctc ttagccctcg tgggtcagag tctctgttgc atattgtctt    8220
ttgttgtttt tcacaacctt ttagaaacat aaaagcatt cttagcccgt gggctggaca     8280
aaaaaaggcc atgacgggct gtatggattt ggcccagcag gcccttgctt gccaagccct    8340
gttttagaca aggagcagct tgtgtgcctg gaaccatcat gggcacaggg gaggagcaga    8400
gtggatgtgg aggtgtgagc tggaaaccag gtcccagagc gctgagaaag acagagggtt    8460
tttgcccttg caagtagagc aactgaaatc tgacaccatc cagttccaga aagccctgaa    8520
gtgctggtgg acgctgcggg gtgctccgct ctagggttac agggatgaag atgcagtctg    8580 gtaggggag tccactcacc tgttggaaga tgtgattaag aaaagtagac tttcagggcc     8640
```

```
gggcatggtg gctcacgcct gtaatcccag cactttggga ggccgaggcg ggtggatcac    8700
gaggtcagga gatcgagacc atcctggcta acatggtgaa accccgtctt tactaaaaat    8760
acaaaaaatt agctgggcgt ggtggcgggc gcctgtagtc ccagctactc gggaggctga    8820
ggcaggagaa tggcgtgaac ctgggaggtg gagcttgctg tgagccgaga tcgcgccact    8880
gcactccagc ctgggcgaca gagcgagact ccgtctcaaa aaaaaaaaa aaagtaggct    8940 ttcatgatgt gtgagctgaa ggcgcagtag gcagaagtag aggcctcagt ccctgcagga    9000
gacccctcgg tctctatctc ctgatagtca gacccagcca cactggaaag aggggagaca    9060
ttacagcctg cgagaaaagt agggagattt aaaaactgct tggcttttat tttgaactgt    9120 ttttttgtt tgtttgtttt ccccaattca gaatacagaa tacttttatg gatttgtttt    9180
tattacttta atttgaaac aatataatct tttttttgtt gttttttga cagggtct    9240 tactctgtca cccaggctga gtgcagtggt gtgatcttgg ctcacctcag cctcgacccc    9300
ctgggctcaa atgattctcc cacctcagct tcccaagtag ctgggaccac aggtgcgtgt    9360
gttgcgctat acaaatcctg aagacaagga tgctgttgct ggtgatgctg gggattccca    9420
agatcccaga tttgatggca ggatgcccct gtctgctgcc ttgccagggt gccaggaggg    9480
cgctgctgtg gaagctgagg cccggccatc cagggcgatg cattgggcgc tgattcttgt    9540
tcctgctgct gcctcggtgc ttagcttttg aaacaatgaa ataaattaga accagtgtga    9600
aaatcgatca gggaataaat ttaatgtgga aataaactga caacttagt tcttcataag    9660 agtttacttg gtaaatactt gtgatgagga caaaacgaag cactagaagg agaggcgagt    9720
tgtagacctg ggtggcagga gtgtttttgtt tgttttcttt ggcagggtct tgctctgttg    9780
ctcaggctgg agtacagtgg cacaatcaca gctcactata gcctcgacct cctggactca    9840
agcaatcctc ctgcctcagc ctcccagtag ctgggactac aggcgcatgc caccatgcct    9900
ggctaatttt aaattttttt ttttctcttt tttgagatgg aatctcactc tgtcgcccag    9960
gctggagtgc agtggcgtga tctcggctga cggcaagctc cgcctcccag gttcactcca    10020
ttcgcctgcc tcagcctccc aagtagctgg gactacaggc gctgggatta caaacccaaa    10080
cccaaagtgc tgggattaca ggcgtgagcc actgcacccg gcctgttttg tctttcaata    10140
gcaagagttg tgtttgcttc gcccctacct ttagtggaaa aatgtataaa atggagatat    10200
tgacctccac attgggtgg ttaaattata gcatgtatgc aaaggagctt cgctaattta    10260 aggcttttt gaaagagaag aaactgaata atccatgtgt gtatatatat tttaaaagcc    10320
atggtcatct ttccatatca gtaaagctga ggctccctgg gactgcagag ttgtccatca    10380
cagtccatta taagtgcgct gctgggccag gtgcagtggc ttgtgcctga atcccagcac    10440
tttgggaggc caaggcagga ggattcattg agcccaggag ttttgaggcg agcctgggca    10500
atgtggccag acctcatctc ttcaaaaaat acacaaaaaa ttagccaggc atggtggcac    10560
gtgcctgtag tctcagctac tcaggaggct gaggtgggag gatcactttg agccttgcag    10620
gtcaaagctg cagtaagcca tgatcttgcc actgcattcc agcctggatg acagagcgag    10680
accctgtctc taaaaaaaaa aaaaaccaaa cggtgcactg ttttcttttt tcttatcaat    10740
ttattatttt taaattaaat tttcttttaa taatttataa attataaatt tatattaaaa    10800
aatgacaaat ttttattact tatacatgag gtaaaactta ggatatataa agtacatatt    10860
gaaaagtaat tttttggctg gcacagtggc tcacacctgt aatcccagca ctttgggagg    10920
ccgtggcggg cagatcacat gagatcatga gttcgagacc aacctgacca acatggagag    10980
```

```
acccccatctc tactaaaaat acaaaattag ccggggtggt ggcgcatgcc tgtaatccca   11040
gctactcggg aggctgaggc aggagaatct cttgaacccg ggaggcagag gttgcggtga   11100
gccaagatcg tgcctttgca caccagccta ggcaacaaga gcgaaagtcc gtctcaaaaa   11160
aaaagtaatt ttttttaagt taacctctgt cagcaaacaa atttaaccca ataaaggtct   11220
ttgtttttta atgtagtaga ggagttaggg tttataaaaa atatggtagg aagggggtc    11280
cctggattg ctaatgtgat tgtcatttgc cccttaggag agagctctgt tagcagaatg    11340
aaaaaattgg aagccagatt cagggaggga ctggaagcaa agaatttct gttcgaggaa    11400
gagcctgatg tttgccaggg tctgtttaac tggacatgaa gaggaaggct ctggactttc   11460
ctccaggagt ttcaggagaa aggtagggca gtggttaaga gcagagctct gcctagacta   11520
gctggggtgc ctagactagc tggggtgccc agactagctg gggtgcctag actagctggg   11580
tactttgagt ggctccttca gcctggacct cggtttcctc acctgtatag tagagatatg   11640
ggagcaccca gcgcaggatc actgtgaaca taaatcagtt aatggaggaa gcaggtagag   11700
tggtgctggg tgcataccaa gcactccgtc agtgtttcct gttattcgat gattaggagg   11760
cagcttaaac tagagggagt tgagctgaat caggatgttt gtcccaggta gctgggaatc   11820
tgcctagccc agtgcccagt ttatttaggt gctctctcag tgttccctga ttgttttttc   11880
ctttgtcatc ttatctacag gatgtgactg ggaagctctg gtttcagtgt catgtgtcta   11940
ttctttatt ccaggcaaag gaaaccaaca ataagaagaa agaatttgag gaaactgcga   12000
agaaagtgcg ccgtgccatc gagcagctgg ctgccatgga ttgaggcctc tggccggagc   12060
tgcctggtcc cagagtggct gcaccacttc cagggtttat tccctggtgc caccagcctt   12120
cctgtgggcc ccttagcaat gtcttaggaa aggagatcaa cattttcaaa ttagatgttt   12180
caactgtgct cctgttttgt cttgaaagtg gcaccagagg tgcttctgcc tgtgcagcgg   12240
gtgctgctgg taacagtggc tgcttctctc tctctctctc tttttgggg gctcattttt    12300
gctgttttga ttcccgggct taccaggtga gaagtgaggg aggaagaagg cagtgtccct   12360
tttgctagag ctgacagctt tgttcgcgtg ggcagagcct tccacagtga atgtgtctgg   12420
acctcatgtt gttgaggctg tcacagtcct gagtgtggac ttggcaggtg cctgttgaat   12480
ctgagctgca ggttccttat ctgtcacacc tgtgcctcct cagaggacag ttttttttgtt  12540
gttgtgtttt tttgttttt tttttgggta gatgcatgac ttgtgtgtga tgagagaatg    12600
gagacagagt ccctggctcc tctactgttt aacaacatgg ctttcttatt ttgtttgaat   12660
tgttaattca cagaatagca caaactacaa ttaaaactaa gcacaaagcc attctaagtc   12720
attggggaaa cggggtgaac ttcaggtgga tgaggagaca gaatagagtg ataggaagcg   12780
tctggcagat actccttttg ccactgctgt gtgattagac aggcccagtg agccgcgggg   12840
cacatgctgg ccgctcctcc ctcagaaaaa ggcagtggcc taaatccttt ttaaatgact   12900
tggctcgatg ctgtggggga ctggctgggc tgctgcaggc cgtgtgtctg tcagcccaac   12960
cttcacatct gtcacgttct ccacacgggg gagagacgca gtccgcccag gtccccgctt   13020
tctttggagg cagcagctcc cgcagggctg aagtctggcg taagatgatg gatttgattc   13080
gccctcctcc ctgtcataga gctgcagggt ggattgttac agcttcgctg gaaacctctg   13140
gaggtcatct cggctgttcc tgagaaataa aaagcctgtc atttcaaaca ctgctgtgga   13200
ccctactggg tttttaaaat attgtcagtt tttcatcgtc gtccctagcc tgccaacagc   13260
catctgccca gacagccgca gtgaggatga gcgtcctggc agagacgcag ttgtctctgg   13320
gcgcttgcca gagccacgaa ccccagacct gtttgtatca tccgggctcc ttccgggcag   13380
```

```
aaacaactga aaatgcactt cagacccact tatttatgcc acatctgagt cggcctgaga    13440 tagactttc  cctctaaact gggagaatat cacagtggtt tttgttagca gaaaatgcac    13500
tccagcctct gtactcatct aagctgctta tttttgatat ttgtgtcagt ctgtaaatgg    13560
atacttcact ttaataactg ttgcttagta attggctttg tagagaagct ggaaaaaaat    13620
ggttttgtct tcaactcctt tgcatgccag gcggtgatgt ggatctcggc ttctgtgagc    13680
ctgtgctgtg ggcagggctg agctggagcc gcccctctca gcccgcctgc cacggccttt    13740
ccttaaaggc catccttaaa accagaccct catggctgcc agcacctgaa agcttcctcg    13800
acatctgtta ataaagccgt aggcccttgt ctaagcgcaa ccgcctagac tttctttcag    13860
atacatgtcc acatgtccat ttttcaggtt ctctaagttg gagtggagtc tgggaagggt    13920
tgtgaatgag gcttctgggc tatgggtgag gttccaatgg caggttagag ccctcgggc    13980 caactgccat cctggaaagt agagacagca gtgcccgctg cccagaagag accagcaagc    14040
caaactggag cccccattgc aggctgtcgc catgtggaaa gagtaactca caattgccaa    14100
taaagtctca tgtggtttta tctacttttt ttttcttttt cttttttttt gagacaaggc    14160
cttgccctcc caggctggag tgcagtggaa tgaccacagc tcaccgcaac ctcaaattct    14220
tgcgttcaag tgaacctccc actttagcct cccaagtagc tgggactaca ggcgcacgcc    14280
atcacacccg gctaattgaa aaattttttt ttttgtttag atggaatctc actttgttgc    14340
ccaggctggt ctcaaactcc tgggctcaag tgatcatcct gcttcagcgt ccgacttgtt    14400
ggtattatag gcgtgagcca ctgggcctga cctagctacc attttttaat gcagaaatga    14460
agacttgtag aaatgaaata acttgtccag gatagtcgaa taagtaactt ttagagctgg    14520
gatttgaacc caggcaatct ggctccagag ctgggccctc actgctgaag gacactgtca    14580
gcttgggagg gtggctatgg tcggctgtct gattctaggg agtgagggct gtctttaaag    14640
caccccattc cattttcaga cagctttgtc agaaaggctg tcatatggag ctgacacctg    14700
cctccccaag gcttccatag atcctctctg tacattgtaa ccttttattt tgaaatgaaa    14760
attcacagga agttgtaagg ctagtacagg ggatcc                             14796
```

<210> SEQ ID NO 5
<211> LENGTH: 260
<212> TYPE: DNA
<213> ORGANISM: Homo sapiens

<400> SEQUENCE: 5

```
ggcagggacg agctggcgcg gcgtcgctgg gtgcaccgcg accacgggca gagccacgcg     60
gcgggaggac tacaactccc ggcacacccc gcgccgcccc gcctctactc ccagaaggcc    120 gcgggggtg  gaccgcctaa gagggcgtgc gctcccgaca tgccccgcgg cgcgccatta    180
accgccagat ttgaatcgcg ggacccgttg gcagaggtgg cggcggcggc atgggtgccc    240
cgacgttgcc ccctgcctgg                                                260
```

<210> SEQ ID NO 6
<211> LENGTH: 230
<212> TYPE: DNA
<213> ORGANISM: Homo sapiens

```
<400> SEQUENCE: 6
ggcagggacg agctggcgcg gcgtcgctgg gtgcaccgcg accacgggca gagccacgcg      60
gcgggaggac tacaactccc ggcacacccc gcgccgcccc gcctctactc ccagaaggcc     120
gcggggggtg gaccgcctaa gagggcgtgc gctcccgaca tgccccgcgg cgcgccatta     180
accgccagat ttgaatcgcg ggacccgttg gcagaggtgg cggcggcggc                230
```